(12) United States Patent
Lemke et al.

(10) Patent No.: US 8,781,571 B2
(45) Date of Patent: Jul. 15, 2014

(54) SWITCH VALIDATION CIRCUIT AND METHOD

(75) Inventors: John Lemke, Pleasanton, CA (US); Scot Satre, Brentwood, CA (US); Corinna X. Chen, Oakland, CA (US); Brian W. Read, Brier, WA (US)

(73) Assignee: Incline Therapeutics, Inc., Redwood City, CA (US)

( * ) Notice: Subject to any disclaimer, the term of this patent is extended or adjusted under 35 U.S.C. 154(b) by 183 days.

(21) Appl. No.: 13/249,975

(22) Filed: Sep. 30, 2011

(65) Prior Publication Data

US 2012/0253262 A1 Oct. 4, 2012

Related U.S. Application Data

(60) Provisional application No. 61/470,340, filed on Mar. 31, 2011.

(51) Int. Cl.
*A61N 1/30* (2006.01)
*H02H 3/20* (2006.01)
*H02H 3/24* (2006.01)

(52) U.S. Cl.
USPC ............................................. 604/20; 361/90

(58) Field of Classification Search
CPC ......... A61N 1/30; A61N 1/325; A61N 1/303; A61N 1/403; A61N 2005/0645; H03K 17/0822; H03K 2017/0806; H03K 17/082; H03K 17/18
USPC ........................................ 604/20; 361/78–92
See application file for complete search history.

(56) References Cited

U.S. PATENT DOCUMENTS

| | | | |
|---|---|---|---|
| 4,141,359 A | 2/1979 | Jacobsen et al. |
| 4,474,570 A | 10/1984 | Ariura et al. |
| 4,588,580 A | 5/1986 | Gale et al. |
| 4,698,582 A | 10/1987 | Braun et al. |
| 4,752,285 A | 6/1988 | Petelenz et al. |
| 4,822,802 A | 4/1989 | Levy et al. |
| 4,878,892 A | 11/1989 | Sibalis et al. |
| 4,931,046 A | 6/1990 | Newman |
| 5,006,108 A | 4/1991 | LaPrade |

(Continued)

FOREIGN PATENT DOCUMENTS

| | | |
|---|---|---|
| EP | 1084729 A2 | 3/2001 |
| GB | 2239803 A | 7/1991 |

(Continued)

OTHER PUBLICATIONS

Ahmed et al.; Fentanyl HCl iontophoretic transdermal system versus intravenous morphine pump after gynecologic surgery; Arch Gynecol Obstet; vol. 276; pp. 251-258; 2007.

(Continued)

*Primary Examiner* — Aarti B Berdichevsky
*Assistant Examiner* — Bradley Osinski
(74) *Attorney, Agent, or Firm* — Shay Glenn LLP

(57) ABSTRACT

A switch operated therapeutic agent delivery device is described. Embodiments of the operated therapeutic agent delivery device include a switch that can be operated by a user, a device controller connected to the switch through a switch input where the device can actuate the device when certain predetermined conditions are met, and a switch integrity subcircuit which is used to detect a fault or a precursor to a fault.

25 Claims, 17 Drawing Sheets

(56) References Cited

U.S. PATENT DOCUMENTS

| | | | |
|---|---|---|---|
| 5,019,034 A | 5/1991 | Weaver et al. | |
| 5,047,007 A | 9/1991 | McNichols et al. | |
| 5,135,477 A | 8/1992 | Untereker et al. | |
| 5,135,479 A | 8/1992 | Sibalis et al. | |
| 5,203,768 A | 4/1993 | Haak et al. | |
| 5,224,927 A | 7/1993 | Tapper | |
| 5,224,928 A | 7/1993 | Sibalis et al. | |
| 5,232,438 A | 8/1993 | Theeuwes et al. | |
| 5,232,448 A | 8/1993 | Zdeb | |
| 5,246,418 A | 9/1993 | Haynes et al. | |
| 5,254,081 A | 10/1993 | Maurer et al. | |
| 5,306,235 A * | 4/1994 | Haynes | 604/20 |
| 5,320,597 A | 6/1994 | Sage, Jr. et al. | |
| 5,358,483 A | 10/1994 | Sibalis | |
| 5,644,463 A | 7/1997 | El-Sharkawi et al. | |
| 5,688,232 A | 11/1997 | Flower | |
| 5,697,896 A * | 12/1997 | McNichols et al. | 604/20 |
| 5,804,957 A | 9/1998 | Coln | |
| 5,983,133 A | 11/1999 | Garde et al. | |
| 6,035,234 A | 3/2000 | Riddle et al. | |
| 6,216,033 B1 | 4/2001 | Southam et al. | |
| 6,385,488 B1 | 5/2002 | Flower et al. | |
| 6,425,892 B2 | 7/2002 | Southam et al. | |
| 6,970,739 B1 | 11/2005 | Inoue | |
| 7,027,859 B1 | 4/2006 | McNichols et al. | |
| 7,302,293 B2 | 11/2007 | Southam et al. | |
| 7,597,679 B2 | 10/2009 | Jespersen et al. | |
| 7,621,893 B2 | 11/2009 | Moberg et al. | |
| 7,766,873 B2 | 8/2010 | Moberg et al. | |
| 2004/0085215 A1 | 5/2004 | Moberg et al. | |
| 2006/0161827 A1 * | 7/2006 | Gohel et al. | 714/736 |
| 2007/0035903 A1 * | 2/2007 | Sullivan et al. | 361/78 |
| 2009/0171502 A1 | 7/2009 | Freidin | |
| 2010/0037680 A1 | 2/2010 | Moberg et al. | |

FOREIGN PATENT DOCUMENTS

| | | |
|---|---|---|
| JP | 07-067971 | 3/1995 |
| JP | 07-124265 | 5/1995 |
| WO | WO 90/03825 A1 | 4/1990 |
| WO | WO 93/01807 A1 | 2/1993 |
| WO | WO 95/27530 A1 | 10/1995 |

OTHER PUBLICATIONS

Chelly, Jacques E.; An intophoretic, fentanyl HCI patient-controlled transdermal system for acute postoperative pain management; Expert Opin. Pharmacother.; vol. 6; No. 7; pp. 1205-1214; 2005.

Grond et al.; Iontophoretic transdermal system using fentanyl compared with patient-controlled intravenous analgesia using morphine for postoperative pain management; British Journal of Anaesthesia; vol. 98; No. 6; pp. 806-815; 2007.

Minkowitz et al.; Safety and tolerability of fentanyl iontophoretic transdermal system: Findings from a pooled data analysis of four clinical trials; Journal of Opioid Management; vol. 6; No. 3; pp. 203-210; May/Jun. 2010.

Sathyan et al.; Passive absorption of fentanyl from the fentanyl HCI iontophoretic transdermal system; Current Medical Research and Opinion; vol. 25; No. 2; pp. 363-366; 2009.

Viscusi, Eugene; Patient-controlled drug delivery for acute postoperative pain management: A review of current and emerging technologies; Regional Anesthesia and Paid Medicine; vol. 33; No. 2; pp. 146-158; Mar.-Apr. 2008.

* cited by examiner

SWITCH VALIDATION CIRCUIT AND METHOD

CROSS REFERENCE TO RELATED APPLICATION

This application claims the benefit under 35 U.S.C. 119 of U.S. Provisional Patent Application No. 61/470,340, filed Mar. 31, 2011, titled "Switch Validation Circuit and Method". This application is herein incorporated by reference in its entirety.

BACKGROUND

A switch operated therapeutic agent delivery device can provide single or multiple doses of a therapeutic agent to a patient by activating a switch. Upon activation, such a device delivers a therapeutic agent to a patient. A patient-controlled device offers the patient the ability to self-administer a therapeutic agent as the need arises. For example, the therapeutic agent can be an analgesic agent that a patient can administer whenever sufficient pain is felt.

One means of patient controlled analgesia is patient controlled intravenous infusion, which is carried out by an infusion pump, which is pre-programmed to respond to the instructions of a patient within certain pre-determined dosing parameters. Such intravenous infusion pumps are commonly used for control of postoperative pain. The patient initiates infusion of a dose of analgesic, which is typically a narcotic, by signaling a control unit. The unit receives the signal and, if certain conditions are met, begins infusion of the drug through a needle that has been inserted into one of the patient's veins.

Another form of patient controlled analgesia is electrotransport (e.g., iontophoresis, also referred to as iontophoretic drug delivery). In electrotransport drug delivery, a therapeutic agent is actively transported into the body by electric current. Examples of electrotransport include iontophoresis, electroosmosis and electroporation. Iontophoresis delivery devices typically comprise at least two electrodes connected to reservoirs, a voltage source, and a controller that controls delivery of the therapeutic agent by applying the voltage across the pair of electrodes. Usually at least one of the reservoirs contains a charged therapeutic agent (drug), while at least one reservoir contains a counter-ion and no therapeutic agent. The therapeutic agent, which is a charged species, is driven from the reservoir containing the therapeutic agent and into and across the skin into the patient to whom the reservoirs are attached.

In addition to therapeutic agent, the reservoirs may contain other charged and uncharged species. For example, the reservoirs are often hydrogels, which contain water as a necessary constituent. The reservoirs may also contain electrolytes, preservatives, antibacterial agents, and other charged and uncharged species.

SUMMARY OF THE DISCLOSURE

The present invention addresses a need in the art of patient-controlled drug administration devices, especially those devices that are subject to humidity and other contaminants during storage and use, such as iontophoresis devices. The inventors have identified contaminants present in storage and use of iontophoresis devices, as being particularly problematic, as they can cause the device to malfunction. For example, in electrotransport, such as iontophoresis—and on-demand drug delivery in general—faulty circuitry can be especially problematic, as it can, in some instances, cause the device to fail to deliver a full dose, to deliver more than the desired dose, to deliver one or more doses during storage, to deliver one or more doses in the absence of a patient instruction, etc. The potential for contamination of electronic circuitry is especially present in iontophoretic drug delivery systems, as the reservoirs employed contain water as well as other charged and uncharged species—such as charged therapeutic agent, electrolytes, preservatives and antibacterial agents—which can contaminate circuitry, such as activation switches, circuit leads, circuit traces, etc. (Other drug delivery methods, such as patient-activated pumps, can present similar potential for contamination, especially with environmental humidity and airborne contaminants.) In combination with voltages and currents applied to the circuitry during drug delivery (and in some cases storage), contaminants can cause current leaks, short circuits ("shorts", including intermittent shorts) and other spurious signals that can interfere with the proper operation of the device. Other causes of circuit malfunction can also be introduced during manufacturing or in the use environment. The inventors have identified a particular part of the circuitry—the activation switch, as a point that is in some cases especially vulnerable to contamination and malfunction. The inventors have further identified the activation switch as a part of the circuitry that is a focal point for detecting and averting potential and actual circuit faults before they negatively impact device performance, and ultimately, patient health.

Embodiments of the device and methods described herein address the issues raised above by providing means to actively seek out and detect circuit faults and precursors to faults. The means employed involve performing active checks of the device circuitry while the device is powered on, e.g. before, during or after drug delivery. Some embodiments of the device and methods described herein provide for active detection of circuit faults and/or precursors to faults after any button push or after any event that mimics a button push, such as a spurious voltage. Some embodiments provide for active detection of circuit faults or precursors to faults, for instance, between button pushes in an activation sequence, during drug delivery, and between drug delivery sequences (i.e. after one dose has been delivered and before commencement of delivery of another dose).

In some embodiments, the active testing during use of the device is in addition to testing during or following device manufacturing.]

Thus there is described herein a therapeutic agent delivery device, such as an electrotransport device (e.g. an iontophoresis device), which comprises a means for containing and delivering the therapeutic agent to a patient, a means for controlling delivery of the therapeutic agent to the patient, a means for detecting one or more faults and/or precursors to faults during device operation, and a means for disabling the device upon detection of a fault or a precursor to a fault. In some embodiments, the device is an iontophoresis device or other electrotransport device. In some embodiments, the device further comprises a means for alerting a patient and/or caregiver that the device has detected a fault and/or precursor to a fault. In some embodiments, the device further comprises a means for alerting a patient and/or caregiver that the device is being disabled. In some embodiments, the alert is at least one audible tone, at least one visual indicator, or a combination of two or more thereof. In some embodiments, the means for containing and delivering therapeutic agent to the patient includes one or more therapeutic agent reservoirs connected to one or more electrodes for applying a current to the reservoirs and actively transporting therapeutic agent across an outer surface of a patient, such as the skin. In some embodiments, the means for detecting a fault or a precursor to a fault is configured to detect a fault in a switch, such as an activation switch, or other circuit component, such as a trace, a connector, a power supply, an integrated circuit, a lead, a chip, a resistor, a capacitor, an inductor or other circuit component. In some embodiments the means for controlling delivery of the therapeutic agent comprises a pre-programmed or programmable integrated circuit controller, such as an ASIC.

In some embodiments, the circuitry described herein is incorporated into a device for delivery of a therapeutic agent (drug) to a patient. In some embodiments, the device is a patient-activated drug delivery device. In some embodiments, the device is an electrotransport drug delivery device. In some embodiments, the drug delivery device is an iontophoretic drug delivery device. In some embodiments, the drug to be delivered is an opioid analgesic. In some embodiments, the opioid analgesic is a pharmaceutically acceptable salt of fentanyl or sufentanil, such as fentanyl hydrochloride.

In some embodiments, the methods described herein are executed by a device controller, especially a controller of a device for delivery of a therapeutic agent (drug) to a patient. In some embodiments, the methods are carried out by the controller during one or more stages of drug delivery—e.g., during the period of time between pushes of an activation button, during delivery of the drug, between delivery sequences, etc. In some preferred embodiments, the testing is carried out after any button push or anything that appears to be a button push. In particularly preferred embodiments, the methods are under active control of the controller, meaning that the controller initiates detection of faults and precursors to faults in the circuitry, e.g. after a button push or anything that appears to be a button push. In some embodiments, upon detection of a fault or precursor to a fault, the controller takes appropriate action, such as setting a fault detection flag, logging the fault in memory for retrieval at a later time, setting a user warning (such as an indicator light and/or audible tone), and/or disabling the device. In this regard, methods for disabling a device upon detection of a fault are described in U.S. Pat. No. 7,027,859 to McNichols et al., which is incorporated herein in its entirety; in particular column 6, line 65 through column 11, line 35 are specifically incorporated by reference as teaching various ways to disable a circuit.

In some embodiments, there is provided a switch operated device, such as a drug delivery device (e.g., a drug delivery pump or iontophoresis device) comprising: (a) a device switch configured to be operated by a user, which provides a switch signal to a switch input of a device controller when operated by a user; (b) the device controller, having said switch input operatively connected to the switch, and configured to receive the switch signal from the switch, the device controller being configured to actuate the device when the switch signal meets certain predetermined conditions and to control and receive signals from a switch integrity test subcircuit; and (c) the switch integrity test subcircuit, which is configured to detect a fault or a precursor to a fault in the switch and provide a fault signal to the controller. When the controller receives a fault signal from the switch integrity test subcircuit, it executes a switch fault subroutine when a fault or a precursor to a fault is detected. In some embodiments, the switch integrity test subcircuit is configured to check for and detect a fault or a precursor to a fault in the switch. In some embodiments, the switch integrity test subcircuit is configured to test for and detect at least one fault or precursor to a fault such as contamination, short circuits, (including intermittent short circuits), compromised circuit components (including malfunctioning resistors, integrated circuit pins, and/or capacitors), etc.

In some embodiments, the switch integrity test subcircuit is configured to test for and detect a voltage (or change in voltage) between the switch input and ground or some intermediate voltage above ground, a short between the switch input and a voltage pull up or some intermediate voltage below the pull up voltage. In some preferred embodiments the switch integrity test subcircuit is configured to test for and detect a voltage (or change in voltage) between the switch input and some intermediate voltage above ground (a low voltage, $V_L$) and/or a short between the switch input and a some intermediate voltage below the pull up voltage (high voltage $V_H$). Thus, the switch integrity test subcircuit is able to detect a non-determinant signal that indicates contamination (e.g. moisture and/or particulates), corrosion, a damaged circuit resistor, a damaged integrated circuit pin, etc. In some embodiments, the switch fault subroutine includes at least one of: activating a user alert feature, logging detection of faults or precursors to faults, deactivating the device, or one or more combinations thereof. In some embodiments, the controller is configured to measure a voltage or a rate of change of voltage at the switch input and execute the switch fault subroutine when the voltage or rate of change of voltage at the switch input fails to meet one or more predetermined parameters. In some embodiments, the device is an iontophoresis delivery device comprising first and second electrodes and reservoirs, at least one of the reservoirs containing therapeutic agent to be delivered by iontophoresis. In some embodiments, the predetermined conditions for actuating the device include the user activating the switch at least two times within a predetermined period of time. In some embodiments, the switch input is pulled up to a high voltage when the switch is open and the switch input is a low voltage when the switch is closed.

Some embodiments described herein provide a method of switch fault detection in a switch operated device, said device comprising: (a) a device switch connected to a switch input of a device controller; (b) the device controller comprising said switch input; and (c) a switch integrity test subcircuit, said method comprising said controller: (i) activating the switch integrity test subcircuit; (ii) detecting a voltage condition at the switch input; and (iii) activating a switch fault subroutine if the voltage condition at the switch input fails to meet one or more predetermined conditions. In some embodiments, the steps of activating the switch integrity test subcircuit and detecting a voltage condition at the switch input are executed continuously or periodically throughout use of the device. In some embodiments, the switch fault subroutine includes, for example, activating a user alert feature, logging detection of faults or precursors to faults, deactivating the device, or one or more combinations thereof. In some embodiments, the voltage condition is a voltage, a change in voltage or both. In some embodiments, the controller detects the voltage at the switch input under conditions in which the voltage should be zero or nearly zero if the switch integrity is within operating norms, and activates the switch fault subroutine if the voltage is significantly higher than zero. In some embodiments, the controller detects the voltage at the switch input under conditions in which the voltage should be equal to a pull up voltage or nearly equal to the pull up voltage if the switch integrity is within operating norms, and activates the switch fault subroutine if the voltage is significantly lower than the pull up voltage. In some embodiments, the controller detects a change in voltage at the switch input under conditions in which the voltage is expected to fall to zero or nearly to zero after within a predetermined period if the switch integrity is within operating norms, and activates the switch fault subroutine if the voltage fails to fall to zero or nearly to zero within the predetermined period. In some embodiments, the controller detects a change in voltage at the switch input under conditions where, the voltage should rise to a pull up voltage or nearly to the pull up voltage within a predetermined period if the switch integrity is within operating norms, and activates the switch fault subroutine if the voltage fails to rise to the pull up voltage or nearly to the pull up voltage within the predetermined period.

Some embodiments described herein provide a switch operated iontophoresis therapeutic agent delivery device, comprising: (a) a power source; (b) first and second electrodes and reservoirs, at least one of the reservoirs containing the therapeutic agent; (c) a device switch, which provides a switch signal to a switch input of a device controller when operated by a user, the device controller, having said switch input operatively connected to the switch, whereby the controller receives the switch signal from the switch, the device controller being operatively connected to a power source that provides power to the first and second electrodes for delivering therapeutic agent to a patient; and (d) a switch integrity test subcircuit, which is configured to detect a fault in the switch and cause the controller to execute a switch fault subroutine when a fault is detected. In some embodiments, the therapeutic agent is an opioid analgesic as described herein, such as fentanyl or sufentanil or a pharmaceutically acceptable salt, analog or derivative thereof.

A method of switch fault detection in a user operated iontophoresis therapeutic agent delivery device, said device comprising: (a) a power source; (b) first and second electrodes and reservoirs, at least one of the reservoirs containing the therapeutic agent; (c) a device switch connected to a switch input of a device controller; (d) the device controller comprising said switch input and configured to control power to the first and second electrodes, thereby controlling delivery of the therapeutic agent; and (e) a switch integrity test subcircuit, said method comprising said controller: (i) activating the switch integrity test subcircuit; detecting a voltage condition at the switch input; and (ii) activating a switch fault subroutine if the voltage condition at the switch input fails to meet one or more predetermined conditions. In some embodiments, the switch fault subroutine includes, for example, activating a user alert, deactivating the device, or both.

INCORPORATION BY REFERENCE

All publications and patent applications mentioned in this specification are herein incorporated by reference to the same extent as if each individual publication or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

Figure 1:
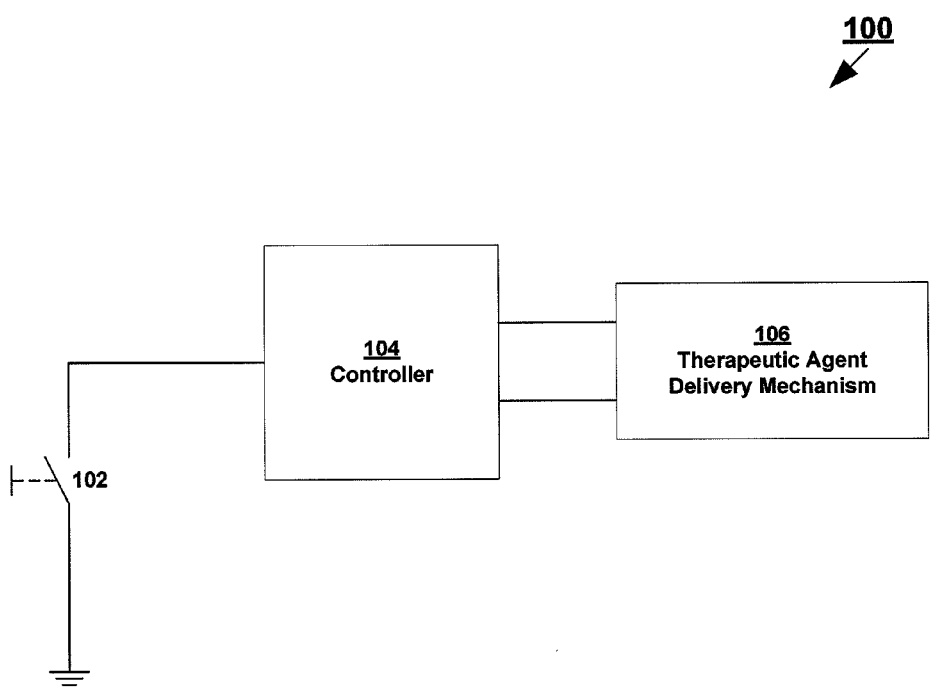
FIG. 1 illustrates an exemplary therapeutic agent delivery system.

Embodiments described herein provide circuitry and methods for actively detecting faults and precursors to faults in devices, such as drug delivery devices, and more particularly iontophoretic drug delivery devices.

In some embodiments, there is provided a switch operated device, such as a drug delivery device (e.g. a drug delivery pump, electrotransport device or iontophoresis device). The device comprises (a) a device switch configured to be operated by a user, which provides a switch signal to a switch input of a device controller when operated by a user; (b) the device controller, having said switch input operatively connected to the switch, and configured to receive the switch signal from the switch, the device controller being configured to actuate the device when the switch signal meets certain predetermined conditions; and (c) a switch integrity test subcircuit, which is configured to detect a fault or a precursor to a fault in the switch, whereby the controller executes a switch fault subroutine when a fault or a precursor to a fault is detected. When the device is an iontophoretic drug delivery device, the device further comprises other circuitry components, such as electrodes, one or more drug also called active reservoirs and one or more counter ion reservoirs which are capable of delivering drug to a patent in response to patient input. An iontophoretic drug delivery device (iontophoresis devices) is illustrated below, though iontophoresis is well-characterized and is described in detail in U.S. Pat. No. 7,027,859, for example.

In some embodiments, the switch integrity test subcircuit is configured to check for and detect a fault or a precursor to a fault in the switch or connecting circuitry. In some preferred embodiments, the act of checking for a fault or precursor to a fault includes setting a circuit condition to evoke a response in the circuit (for example, change in voltage, change in current) which is expected to fall within predetermined parameters if the circuit and its components are free of faults or precursors to faults. In some embodiments, the switch integrity test subcircuit is configured to test for and detect at least one fault or precursor to a fault, such as a member of the group selected from the group consisting of contamination, shorts, (including intermittent short circuits), compromised circuit components (including malfunctioning resistors, integrated circuit pins or interfaces, and/or capacitors), etc. Among the advantages of the device and methods described herein, there may be mentioned the ability to detect and respond to precursors to faults before they manifest in such a manner as to cause the device to malfunction in a way to compromise patient comfort, safety and/or compliance. This aspect of device and methods is described in more detail herein, but includes the ability to actively test for and detect subtle deviations in circuit characteristics from predetermined normal circuit characteristics.

In some embodiments, the switch integrity test subcircuit is configured to test for and detect a voltage or change in voltage in between a short between the switch input and ground or some intermediate voltage above ground (low voltage, $V_L$), a short between the switch input and a voltage pull up or some intermediate voltage below a pull up voltage (high voltage, $V_H$). In some preferred embodiments, the switch integrity test subcircuit is configured to test for and detect a voltage or change in voltage in between a short between the switch input and some intermediate voltage above ground (low voltage, $V_L$) and/or a short between the switch input and intermediate voltage below a pull up voltage (high voltage, $V_H$). Thus, the switch integrity test subcircuit is configured to test for and detect a damaged circuit resistor, contamination (e.g., humidity, particulates), corrosion and/or a damaged integrated circuit pin or integrated circuit interfaces, etc. In particular embodiments, the switch integrity test subcircuit includes the controller and additional circuit components under control of the controller, which the controller is capable of placing in certain states to cause certain effects in the circuit. By detecting the effects that arise when the controller places the circuit components in those predetermined states, and comparing the effects to those which are considered normal for the device, the controller can detect faults and precursors to faults in the device circuitry. It is a particular advantage of the instant device and methods that precursors to faults may be detected before they have manifested in such a way that their effects would be experienced by a patient.

When the switch integrity test subcircuit detects a fault or a precursor to a fault, it provides a fault signal to the controller, which in turn executes a switch fault subroutine, which includes, for example, at least one of: activating a user alert feature, logging detection of faults or precursors to faults, deactivating the device, or one or more combinations thereof. The user alert feature can include a variety of means to alert a user that operation of the system is considered compromised. Since the device is configured, in some embodiments, to detect precursors to faults, the device may activate the user alert even before a fault has been detected that would cause an effect that would be experienced by the patient. The user alert may be an indicator light, such as a colored light emitting diode (LED), an audible tone (such as a repeating "beep"), a readable display (such as a liquid crystal display (LCD)), other user observable indicator (such as a text message, email, voicemail, or other electronic message sent to a device that is observable by the patient, the caregiver or both), or combinations of two or more thereof.

As used herein, unless otherwise defined or limited, the term "when" indicates that a subsequent event occurs at the same time as or at some time after a predicate event. For the sake of clarity, "switch integrity test subcircuit detects a fault or a precursor to a fault, it provides a fault signal to the controller, which in turn executes a switch fault subroutine . . . " is intended to indicate that the subsequent act of executing the switch fault subroutine happens as a consequence of (e.g., at the time of, or at some time after) the predicate event of detection of the fault or precursor to the fault. The term "when" is intended to have analogous effect throughout this disclosure unless otherwise indicated.

In some embodiments, the controller can also log detection of faults or precursors to faults in memory, such as flash memory. In some such embodiments, the controller detects a certain type of fault, assigns it a fault code, and records the fault code in memory for retrieval at a later time. For instance, the controller may detect and record one of the following conditions: a low voltage at a point and under conditions where a high voltage would be expected for a normally operating circuit; a voltage at a point and under conditions that is higher or lower than the voltage that would be expected for a normally operating circuit; a voltage rise time that is longer or shorter than would be expected for a normally operating circuit; a voltage fall time that is longer or shorter than would be expected for a normally operating circuit; or combinations of two or more thereof.

In some embodiments, the switch fault subroutine includes deactivating the device. Methods of deactivating a device, e.g. by irreversibly decoupling the voltage supply from the drug delivery circuit, shorting a power cell to ground, fusing a fusible link in the circuit, etc., are known. In some embodiments, the circuitry and methods employed in U.S. Pat. No. 7,027,859, which incorporated herein by reference, especially those recited between line 65 of column 6 and line 12 of column 8 of U.S. Pat. No. 7,027,859 (and the accompanying figures) may be adapted to disable the circuit when the controller detects a voltage or current, or change thereof, that is outside of predetermined parameters.

In some preferred embodiments, devices and methods taught herein will be capable of performing two or more of the functions of activating a user alert feature (e.g. activating a light and/or audible sound), logging the detected fault or precursor to a fault, and/or deactivating a device. In some preferred embodiments, the devices and methods taught herein are capable of activating a user alert feature, deactivating the device and optionally logging the detected fault or precursor to a fault.

In some embodiments, the controller is configured to measure a voltage or a rate of change of voltage at the switch input and execute the switch fault subroutine when the voltage or rate of change of voltage at the switch input fails to meet one or more predetermined parameters. In some embodiments, the device is an iontophoresis delivery device comprising first and second electrodes and reservoirs, at least one of the reservoirs containing therapeutic agent to be delivered by iontophoresis. It is to be understood that the terms "higher" and "lower" are relative. Especially in embodiments in which the device is capable of detecting and responding to precursors to faults, the terms "higher" and "lower" may express deviations of as little as 10%, 5%, 2% or 1% of the expected values. For example, in terms of voltages, a voltage that is higher than expected may be greater than from 10-200 mV, 10-100 mV, 10-50 mV, 20-200 mV, 20-100 mV, 20-50 mV, 50-200 mV, 50-100 mV, or 100-200 mV higher than the nominal voltage expected at the point and under the conditions tested. In particular, the "higher" voltage may be greater than 10 mV, 20 mV, 50 mV, 75 mV, 100 mV, 125 mV, 150 mV, 175 mV, 200 mV or 250 mV than would be expected at the same point under the conditions tested. Also in terms of voltages, a voltage that is lower than expected may be at least from 10-200 mV, 10-100 mV, 10-50 mV, 20-200 mV, 20-100 mV, 20-50 mV, 50-200 mV, 50-100 mV, or 100-200 mV lower than the voltage expected at the point and under the conditions tested. In particular, the "lower" voltage may be at least 10 mV, 20 mV, 50 mV, 75 mV, 100 mV, 125 mV, 150 mV, 175 mV, 200 mV or 250 mV less than would be expected at the same point under the conditions tested. Voltage rise and fall times may be characterized in the amount of time necessary (e.g., measured in ms or μs) for a point under a condition tested to achieve an expected voltage state. In terms of rise or fall times, the difference in rise or fall time from the expected rise or fall time may be as little as 1 ms or as much as 20 ms, e.g. 1, 2, 5, 10, 12.5, 15 or 20 ms, depending upon the point tested under the particular conditions. Voltage and current rise times may also be characterized by measuring a change in voltage or current between two selected time points and comparing them to the change in voltage or current that would be expected for a normally operating circuit at the point and under the condition tested.

In some preferred embodiments, the device is capable of detecting subtle differences in circuit states—whether voltages, currents, changes in voltages or changes in currents. These subtle changes may indicate that the circuit board has been contaminated with one or more contaminants, is experiencing intermittent shorts between circuit components, has one or more compromised circuit components, or combinations thereof. Such embodiments permit the device to identify precursors to faults before they manifest as circuit faults that can affect delivery of a drug and in particular before they are noticed by, or affect, a patient.

In some embodiments, the predetermined conditions for actuating the device include the user activating the switch at least two times within a predetermined period of time. This feature permits the device to distinguish between purposeful activation of the switch by a user (patient or caregiver, preferably a patient) and spurious or accidental button pushes, e.g. those that occur during shipping or storage, those that occur from contamination, or those that may accidentally occur during placement of the device on the patient or during movement of the patient after the device has been applied to the patient. Activation of the switch by multiple button pushes or the like is described with reference to the figures herein. The time between button pushes—which is typically on the order of at least a few hundred milliseconds (ms)—affords one time window during which the device controller can actively test the switch circuit. In some embodiments, the device is configured such that the device will initiate drug delivery when it receives two distinct button pushes of a predetermined separation in time—e.g. on the order of 100-400 ms, preferably about 300 ms. During this period, which may be referred to as the debounce period, the controller can actively set certain circuit parameters (using the switch integrity test subcircuit), test voltages or changes in voltages at certain points and compare them to predetermined values that are indicative of what a normally operating circuit—i.e. a circuit that is not manifesting a fault or a precursor to a fault—would manifest. For example, the controller may set a switch input to a low state and remove a high supply voltage ($V_{DD}$), then check whether the switch input achieves a true low (expected) of 0 mV above the low supply voltage ($V_{SS}$, e.g., ground or some voltage above ground), or if it fails to achieve such a true low (indicating a fault or precursor to a fault) of at least 5 mV to at least 250 mV above $V_{SS}$ (e.g. at least 5, 10, 15, 20, 25, 30, 35, 40, 45, 50, 75, 100, 125, 150, 200, 225 or 250 mV above $V_{SS}$). If a fault or precursor to a fault is detected, the device controller will then initiate a switch fault subroutine, as described elsewhere herein.

As used herein, $V_{DD}$ refers to any predetermined high voltage ($V_H$), and need not be the highest voltage available from the power supply. Likewise, $V_{SS}$ refers to any predetermined low voltage ($V_L$) and need not indicate "ground". Among other advantages, one advantage of the device and method described herein is that intermediate voltages may be used to test switch integrity, which allows for detection of spurious voltages that indicate contaminants (e.g. humidity, particulates, corrosion, etc.) and other faults and precursors to faults. The precise values of $V_{DD}$ and $V_{SS}$ are selected by the artisan during device design.

In other exemplary embodiments, for example, the controller may set a switch input to a $V_{DD}$ (e.g. a value of from 2 V to 15 V, such as 5 V or 10 V) and connect the switch input to $V_{SS}$ (e.g. a value of 0 V to 1 V above ground), then check whether the switch input achieves $V_{DD}$ (as expected), or if it fails to achieve $V_{DD}$ (indicating a fault or precursor to a fault) by at least 5 mV to at least 250 mV lower than $V_{DD}$ (e.g. at least 5, 10, 15, 20, 25, 30, 35, 40, 45, 50, 75, 100, 125, 150, 200, 225 or 250 mV lower than $V_{DD}$).

In some embodiments, the switch input is pulled up to $V_{DD}$ when the switch is open and the switch input is $V_{SS}$ when the switch is closed. Other configurations are possible. For example, with a change in the logic of the controller, the switch input could be biased to $V_{SS}$, meaning that upon a button push the switch input would be pulled high. The person of skill in the art will recognize that other configurations, including those requiring three, four or more sequential button pushes may be employed, though in general the inventors consider two to be sufficient for most purposes.

Some embodiments described herein provide a method of switch fault detection in a switch operated device, said device comprising: (a) a device switch connected to a switch input of a device controller; (b) the device controller comprising said switch input; and (c) a switch integrity test subcircuit, said method comprising said controller: (i) activating the switch integrity test subcircuit; (ii) detecting a voltage condition at the switch input; and (iii) activating a switch fault subroutine if the voltage condition at the switch input fails to meet one or more predetermined conditions. These methods may be carried out using for example those circuits and devices described herein.

In some embodiments, the steps of activating the switch integrity test subcircuit and detecting a voltage condition at the switch input are executed continuously or periodically throughout operation of the device. Without limitation, such a method may include digital or analog testing. Digital testing is relatively fast and is well-suited to performance during the debounce period between button pushes. Analog testing may be either fast or slow, depending upon how many data points are collected. Analog testing may be, and in some embodiments is, more sensitive and is well-adapted for detection of very subtle deviations from expected device parameters which are symptomatic of precursors to faults. Fast analog testing is well-suited for detection after any button bounce or anything (any voltage signal) that looks like (could be interpreted by the controller as) a button push. Analog testing is also well-suited for the period when drug is being delivered to a patient (that is after the second button press in the case where the device is activated by two distinct button presses) or even during the period between drug delivery intervals (that is when the device is still attached to the patient but is not currently delivering drug). In the latter case, the device may administer a very small amount of current for a brief period of time (e.g. 500 ms to 10 seconds, more preferably 500 ms to 5 seconds, even more preferably 500 ms to 1 second) during which time the controller carries out its active checking. As described herein, analog checking, whether between button pushes, during the dosing period or between dosing periods, is very sensitive and may detect subtle changes in circuit properties before they develop into full-fledged faults, thus permitting avoidance of untoward events before they can manifest. In some embodiments, testing may include a combination of digital and analog testing. In some preferred embodiments, a fast analog test is conducted after any button push (including detection by the controller of any voltage signal that it interprets as a button push) and/or a digital test is conducted after a second button push. In some preferred embodiments, a fast analog test is conducted after any button push (including detection by the controller of any voltage signal that it interprets as a button push) and a digital test is conducted after a second button push. In some embodiments, a slow analog test is conducted in addition to the digital test sometime after the second button push.

Some embodiments described herein provide a switch operated iontophoresis therapeutic agent delivery device, comprising: (a) a power source; (b) first and second electrodes and reservoirs, at least one of the reservoirs containing the therapeutic agent; (c) a device switch, which provides a switch signal to a switch input of a device controller when operated by a user; the device controller having said switch input operatively connected to the switch, whereby the controller receives the switch signal from the switch, the device controller being operatively connected to a power source that provides power to the first and second electrodes for delivering therapeutic agent to a patient; and (d) a switch integrity test subcircuit, which is configured to detect a fault in the switch and cause the controller to execute a switch fault subroutine when a fault is detected. In some embodiments, the therapeutic agent is fentanyl or sufentanil. For the sake of clarity, "fentanyl" includes pharmaceutically acceptable salts of fentanyl, such as fentanyl hydrochloride and "sufentanil" includes pharmaceutically acceptable salts of sufentanil.

Some embodiments described herein provide a method of switch fault detection in a user operated iontophoresis therapeutic agent delivery device, said device comprising: (a) a power source; (b) first and second electrodes and reservoirs, at least one of the reservoirs containing the therapeutic agent; (c) a device switch connected to a switch input of a device controller; (d) the device controller comprising said switch input and configured to control power to the first and second electrodes, thereby controlling delivery of the therapeutic agent; and (e) a switch integrity test subcircuit, said method comprising said controller: (i) activating the switch integrity test subcircuit; detecting a voltage condition at the switch input; and (ii) activating a switch fault subroutine if the voltage condition at the switch input fails to meet one or more predetermined conditions. In some embodiments, the switch fault subroutine includes activating a user alert, deactivating the device, or both.

The present invention relates generally to apparatus (e.g., electrical circuits) which are used to enhance the safety of electrophoretic drug delivery. Drugs having particular potential for use iontophoretic drug delivery include natural and synthetic narcotics. Representative of such substances are, without limitation, analgesic agents such as fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone and cocaine. In the context of iontophoresis, it is to be understood that when reference is made to a drug, unless otherwise stated, it is intended to include all pharmaceutically acceptable salts of the drug substance. For example, where reference is made to fentanyl, the inventors intend that term to include fentanyl salts that are suitable for delivery by iontophoresis, such as fentanyl hydrochloride. Other exemplary pharmaceutically acceptable salts will be apparent to the person having ordinary skill in the art.

For the sake of clarity, as used herein, the terms "therapeutic agent" and "drug" are used synonymously, and include both approved drugs and agents which, when administered to a subject, are expected to elicit a therapeutically beneficial effect. For the sake of further clarity, where a particular drug or therapeutic agent is recited, it is intended that that recitation include the therapeutically effective salts of those therapeutic agents.

Reference is now made to the figures, which illustrate particular exemplary embodiments of the device and methods taught herein. The person having skill in the art will recognize that modifications and various arrangements of the illustrated circuits and methods are within the scope of the instant disclosure and claims.

FIG. 1 illustrates an exemplary therapeutic agent delivery system. Therapeutic agent delivery system 100 comprises activation switch 102, controller 104 and therapeutic agent delivery mechanism 106. Activation switch 102 can be selected from a variety of switch types, such as push buttons switch, slide switches and rocker switches. In some embodiments, a push button switch is used. Though either a "momentary on" or "momentary off" push button switch can be used, for the sake of clarity, a momentary on push button switch is given in each example. Controller 104 controls the administration of drugs to the patient as to the specific rate and amount a drug is dispensed. It can also be used to regulate the dosing interval. For example, for a pain medication, the controller could allow a patient to receive a dose at most once in a predetermined time period, e.g. once every five minutes, ten minutes, 15 minutes, 20 minutes, one hour or two hours. Controller 104 can also comprise a power source, such as a battery, or can simply regulate a power source external to the controller. Typically, the power source controlled by controller 104 is used to drive the delivery of the therapeutic agent through therapeutic agent delivery mechanism 106. Controller 104 can be implemented in a number of ways known in the art. It can comprise a microprocessor and memory containing instructions. Alternatively, it can comprise an appropriately programmed field-programmable gate array (FPGA). It can be implemented in discreet logic or in an application specific integrated circuit (ASIC).

Therapeutic agent delivery mechanism 106 can be selected from a variety of dosing mechanisms including iontophoresis and IV-line pumps. In the former case, a small electric charge which is controlled by controller 104 is used to deliver a drug through a patient's skin. In the latter case, the controller 104 controls a pump which introduces the drug into a intravenous line. For the sake of clarity, the examples herein refer to an iontophoretic drug dispenser.

Figure 2:
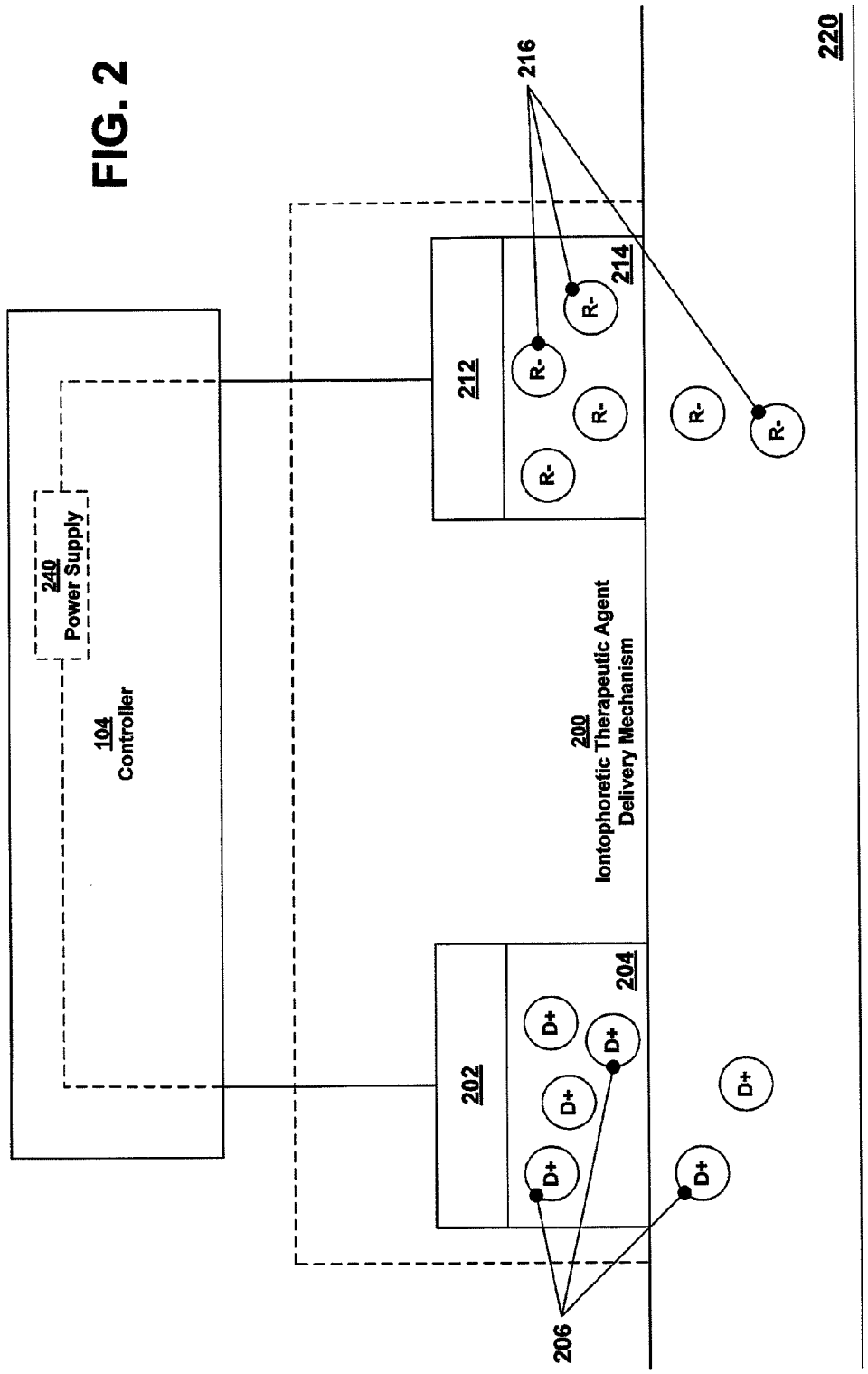
FIG. 2 shows an embodiment of iontophoretic therapeutic agent delivery mechanism.

FIG. 2 shows an embodiment of iontophoretic therapeutic agent delivery mechanism. Iontophoretic therapeutic agent delivery mechanism 200 comprises active electrode 202, active reservoir 204, return electrode 212, counter ion reservoir 214. Active electrode 202 and return electrode 212 are electrically coupled to controller 104. Iontophoretic therapeutic delivery agent delivery mechanism 200 often takes the form of a patch which is attached to the skin of a patient (220). Active reservoir 204 contains ionic therapeutic agent 206, which can be a drug, medicament or other therapeutic agent as described herein and has the same polarity as the active electrode. Counter ion reservoir 214 contains counter ion agent 216, which is an ionic agent of the opposite polarity as the ionic therapeutic agent which can be saline or an electrolyte. In other embodiments, iontophoretic therapeutic delivery mechanism 200 can further comprise additional active and/or counter ion reservoirs.

When controller 104 applies a voltage across active electrode 202 and return electrode 212, the patient's body completes a circuit. The electric field generated in this fashion conducts ionic therapeutic agent 206 from active reservoir 204 into the patient. In this example, controller 104 comprises power supply 240 which can be a battery. In other embodiments controller 104 controls an external power source. Therapeutic agent delivery mechanism 200 often comprises a biocompatible material, such as textiles or polymers, which are well known in the art as well as an adhesive for attaching it to a patient's skin.

In some embodiments, controller 104 and iontophoretic therapeutic agent delivery mechanism 200 are assembled together at the time of application of the therapeutic agent. This packaging permits ready application and insures the integrity of the therapeutic agent, but can also introduce addition points of failure of the delivery device.

Therapeutic agent delivery system 100 is often used in circumstances which allow a patient to self-administer drug. For example, an analgesic agent (such as fentanyl or sufentanil, especially in form of a hydrochloride or other deliverable salt) may be self-administered using such a device. In such a circumstance, a patient can self-administer the analgesic agent whenever he feels pain, or whenever the patient's pain exceeds the patient's pain tolerance threshold. Numerous safeguards and safety features are incorporated into controller 104, in order to ensure the patient's safety. In order to ensure proper delivery in an iontophoretic therapeutic agent delivery system, the device may be configured to take into account the varying resistance of the patient's skin among other elements in the circuit. Thus, controller 104 can regulate the amount of current delivered to the patient in order to permit consistent delivery of the therapeutic agent, by monitoring the current (e.g., by measuring the voltage across a current sensing resistor) and adjusting the voltage up or down accordingly. Furthermore, if the condition of the voltage supply prevents proper operation (e.g., weak battery), the device can shut down.

In operation, it is often convenient for the patient who is not acquainted with the particulars of drug application, and who may also be in painful distress, to allow a button press to activate the delivery of the therapeutic agent. Controller 104 upon activation can administer a single dose at the prescribed rate. To prevent inadvertent dosing, controller 104 can require the patient to activate activation switch 102 twice within a predetermined interval. As previously described, a predetermined debounce interval can be used to insure that a single switch activation attempt by the patient is not incorrectly interpreted as two switch activation attempts. As described herein, this debounce interval provides one convenient period during which a device as described herein can detect and respond to a fault or a precursor to a fault, e.g. using an analog or digital fault checking method.

Figure 3:
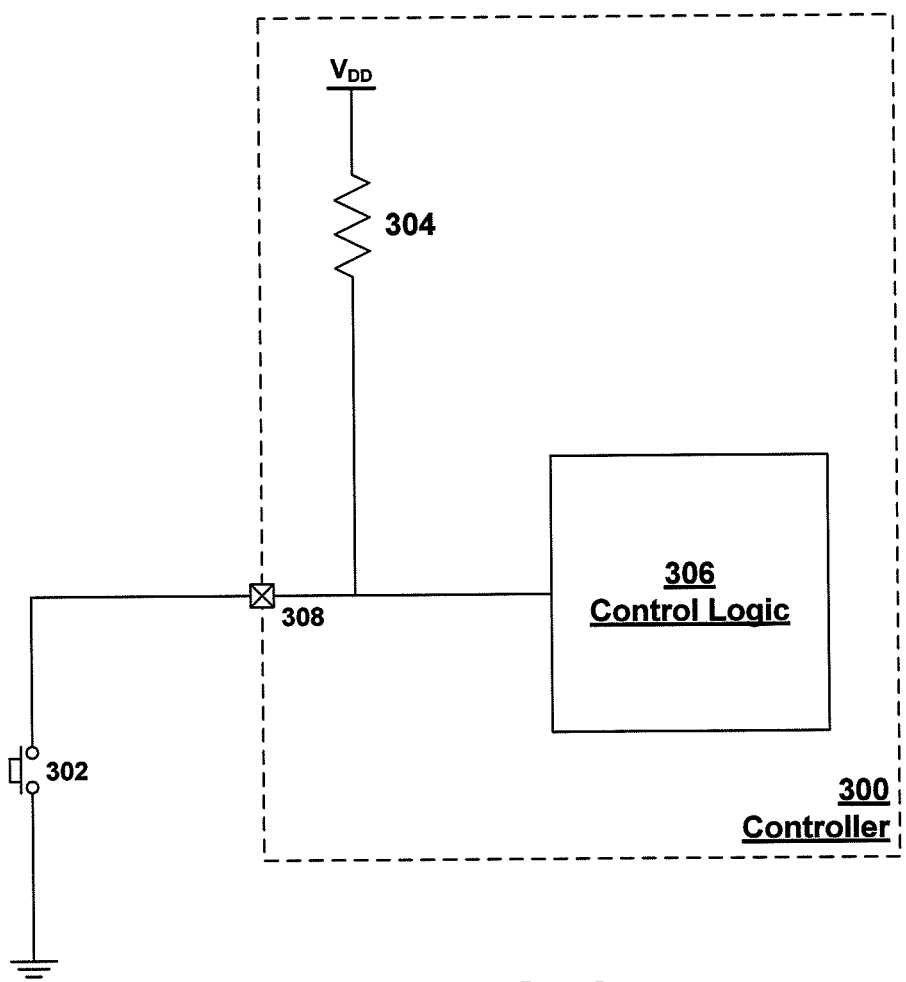
FIG. 3 shows an exemplary embodiment of a controller as connected to an activation switch.

FIG. 3 shows an exemplary embodiment of a controller as connected to an activation switch. Activation switch 302 is shown as a push button momentary "on" switch and is coupled to the ground plane and to controller 300 through switch input 308. Controller 300 comprises pull up resistor 304 and control circuit 306. Pull up resistor 304 is coupled to a supply voltage $V_{DD}$ and switch input 308. Control circuit 306 is also coupled to switch input 308. When activation switch 302 is open, pull up resistor 304 pulls the voltage at switch input 308 to the level of the supply voltage $V_{DD}$. When the activation switch 302 is closed, it pulls the voltage at switch input 308 down to ground.

Although for the sake of illustration reference is made here to $V_{DD}$, $V_{SS}$ and "ground" it is to be understood that wherever reference is made to $V_{DD}$, unless otherwise specified, this is intended to include any predetermined logic level high ($V_H$). Likewise, wherever reference is made to $V_{SS}$ or "ground", it is intended, unless otherwise specified, to include any predetermined logic level low ($V_L$). In some preferred embodiments, the logic high level is an intermediate voltage below $V_{DD}$ and/or the logic low level is some intermediate voltage above ground. In some preferred embodiments, in fact, the logic high level is an intermediate voltage below $V_{DD}$ and the logic low level is some intermediate voltage above ground. For the sake of clarity, in some places herein the logic high may be referred to as $V_H$ and the logic low may be referred to as $V_L$. The use of $V_H$ below $V_{DD}$ and/or $V_L$ above ground (or $V_{SS}$) permits the detection of indeterminate voltage signals that arise out of contamination, corrosion or other faults and precursors to faults.

Figure 4:
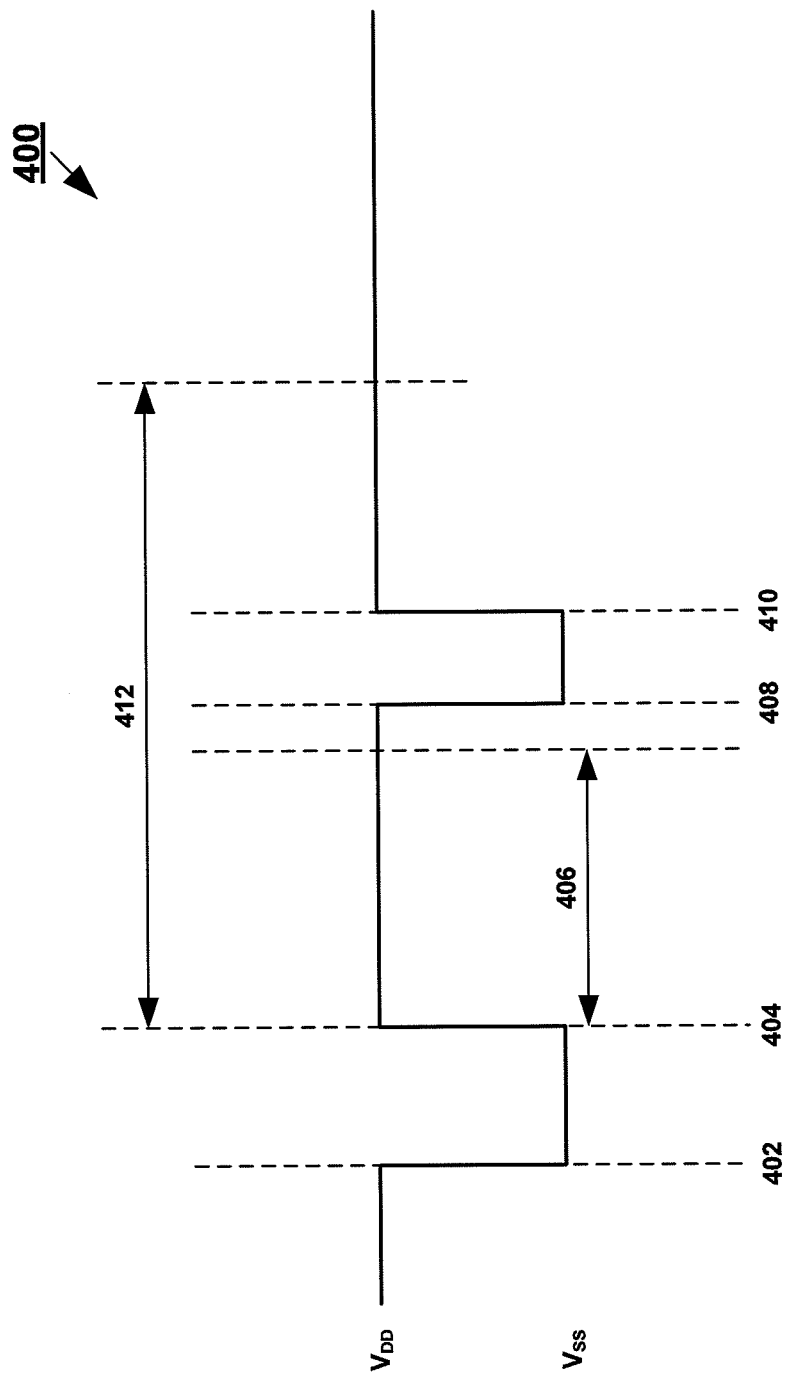
FIG. 4 shows exemplary timing of an activation sequence.

FIG. 4 shows exemplary timing of an activation sequence. Trace 400 shows a plot of voltage at the switch input as a function of time. At time 402, the push button is depressed causing the voltage at switch input 308 to drop to the ground potential. At time 404, the push button is released causing the voltage at switch input 308 to return to the supply voltage level. To further enhance the robustness of the activation of the device, controller 300 enforces a predetermined minimum time interval 406 and a predetermined maximum time interval 412 between the release of the button after the first button press and the second pressing of the button. Should a button press occur before predetermined minimum time interval 406 has elapsed, it is ignored, as during this period it is not clear as to whether a second button press was intended or not. This interval is long enough to avoid an accidental reading, but sufficiently short that an average patient would have a difficult time pressing the button faster than the predetermined minimum time interval. Exemplary predetermined minimum time intervals are given in the overview discussed above. At time 408, which occurs after predetermined minimum time interval has elapsed, a second button press occurs, followed by a button release at time 410. Upon validating the second button press after time 410, controller 300 accepts the sequence as a valid activation sequence and the delivery of the therapeutic agent can begin, provided the second button press is completed before the predetermined maximum time interval has elapsed, for example within 3 seconds. This ensures that an accidental first button press does not leave the therapeutic agent delivery device armed so a second accidental button press could activate the delivery of the therapeutic agent. The activation sequence ensures the therapeutic agent is not delivered accidentally. In addition to ensuring that the therapeutic agent is only delivered when the patient desires it, controller 300 can also incorporate logic and/or circuitry which prevent over-dosing of the therapeutic agent as well as prevent the dispensing of the therapeutic agent after a predetermined lifetime. Such logic and circuitry are described for instance in U.S. Pat. No. 7,027,859, which is incorporated by reference in its entirety, especially as described elsewhere herein. Again, although $V_{DD}$ and $V_{SS}$ are used for illustrative purposes in FIG. 4, any logical high ($V_H$) can be used instead of $V_{DD}$ and any logical low ($V_L$) can be used instead of $V_{SS}$. In some embodiments $V_H<V_{DD}$ or $V_L>V_{SS}$. In some embodiments $V_H<V_{DD}$ and $V_L>V_{SS}$.

Additional safeguards to ensure the integrity of the switch can also be implemented into controller 300. For example, controller 300 can detect whether there is a short (including an intermittent short) between switch 302 and either the ground plane or a power supply trace, which can result from contamination or corrosion. The short circuit can be a "hard" short or an intermittent short. Shorts, including intermittent shorts, can be caused by, for example, corrosion or contamination on the circuit. The corrosion or contamination can provide an electrical pathway, which may be continuous or spurious. Additionally, controller 300 can detect whether there is damage to the switch input, which could be an integrated circuit pin or integrated circuit interface pad. A short due to contamination or corrosion, especially an intermittent short, may not necessarily cause the device to malfunction per se. Initially, the contamination or corrosion can manifest itself in a high resistance path between switch 302 and the ground plane or power supply trace; but over time, as the contamination or corrosion accumulates, the resistance of this path may decrease until ultimately the switch may fail. Therefore, the presence of even a high resistance short is indicative of a future fault. Accordingly, in some embodiments, the controller will detect intermittent shorts such as those described and initiate a suitable switch fault subroutine, as described herein. For example, the switch fault subroutine may include setting one or more suitable user alerts (e.g. and audible tone or a visible indicator) and/or disabling the device (e.g. by disconnecting the power supply from the electrodes).

Figure 5:
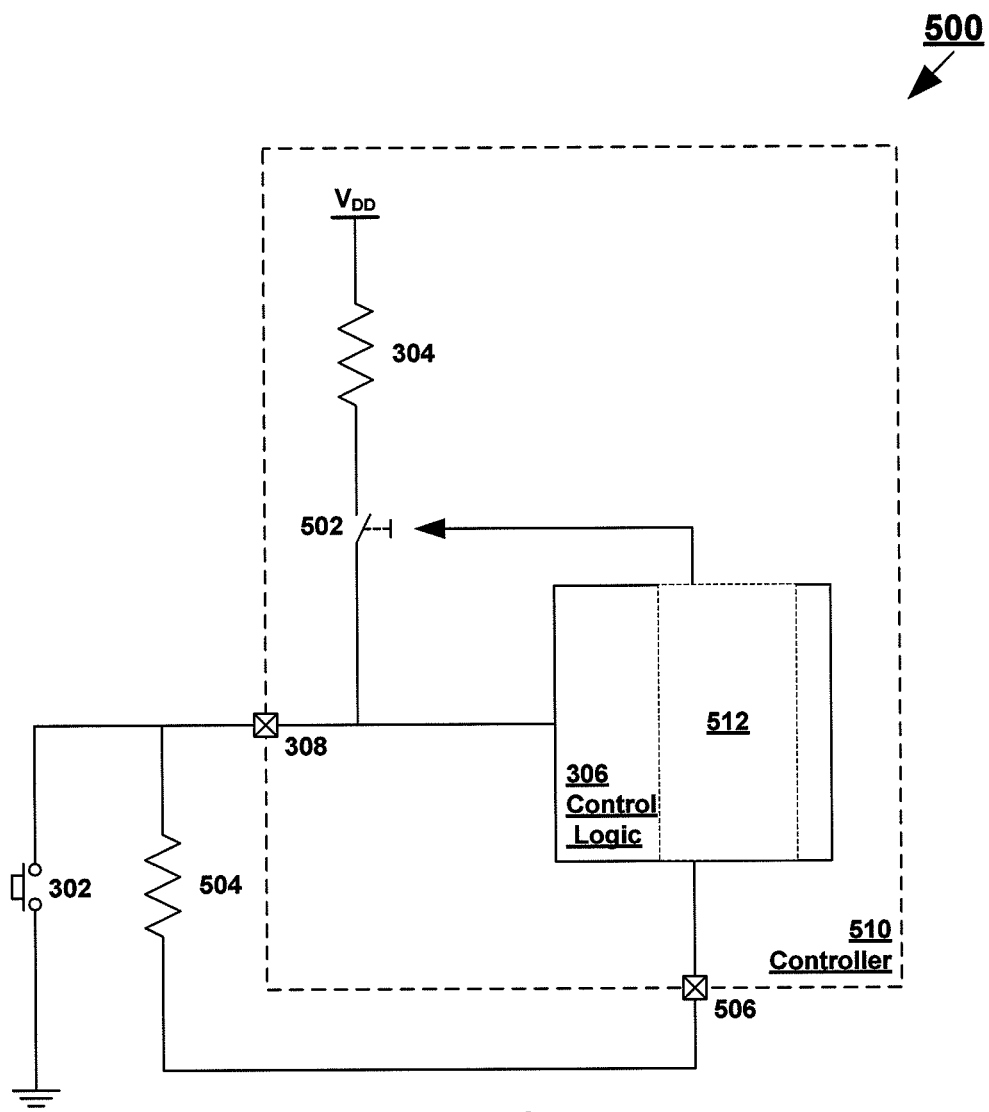
FIG. 5 is an exemplary embodiment of a therapeutic agent delivery device having switch integrity testing.

FIG. 5 is an exemplary embodiment of a therapeutic agent delivery device embodying switch integrity testing. Like controller 300, controller 510 comprises control logic 306, pull up resistor 304, and switch input 308. Controller 510 further comprises a switch integrity test subcircuit comprising switch 502 (which can be used to electrically decouple pull up resistor 304 from switch input 308), switch integrity test output 506 and integrity test sublogic 512 within control logic 306. Switch integrity test subcircuit is activated when switch integrity testing is performed. Integrity test sublogic 512 is configured to open switch 502 and set switch integrity output 506 to a predetermined voltage or sequence of voltages in accordance with a particular switch integrity test. In an implementation where controller 510 resides on an integrated circuit, switch integrity test output 506 can be implemented with a general purpose I/O port or an analog outline pin. Switch integrity test output 506 is coupled to switch input 308 with resistor 504 which generally has a high resistance (e.g., 1 MΩ). Switch integrity test output 506 can be left floating, can provide a high supply voltage ($V_{DD}$) or can provide a low supply voltage ($V_{SS}$) (e.g., ground potential). During testing, switch 502 is opened electrically, decoupling pull up resistor 304 from switch input 308. Depending on the desired test, switch integrity test output 506 provides a high supply voltage or a low supply voltage. Greater detail is given in the following description. For clarity integrity test sublogic 512 is omitted from further diagrams. Again, although $V_{DD}$ and ground are used for illustrative purposes in FIG. 5, any logical high ($V_H$) can be used instead of $V_{DD}$ and any logical low ($V_L$) can be used instead of ground. In some embodiments $V_H<V_{DD}$ or $V_L>$ ground. In some embodiments $V_H<V_{DD}$ and $V_L>$ ground.

Figure 6:
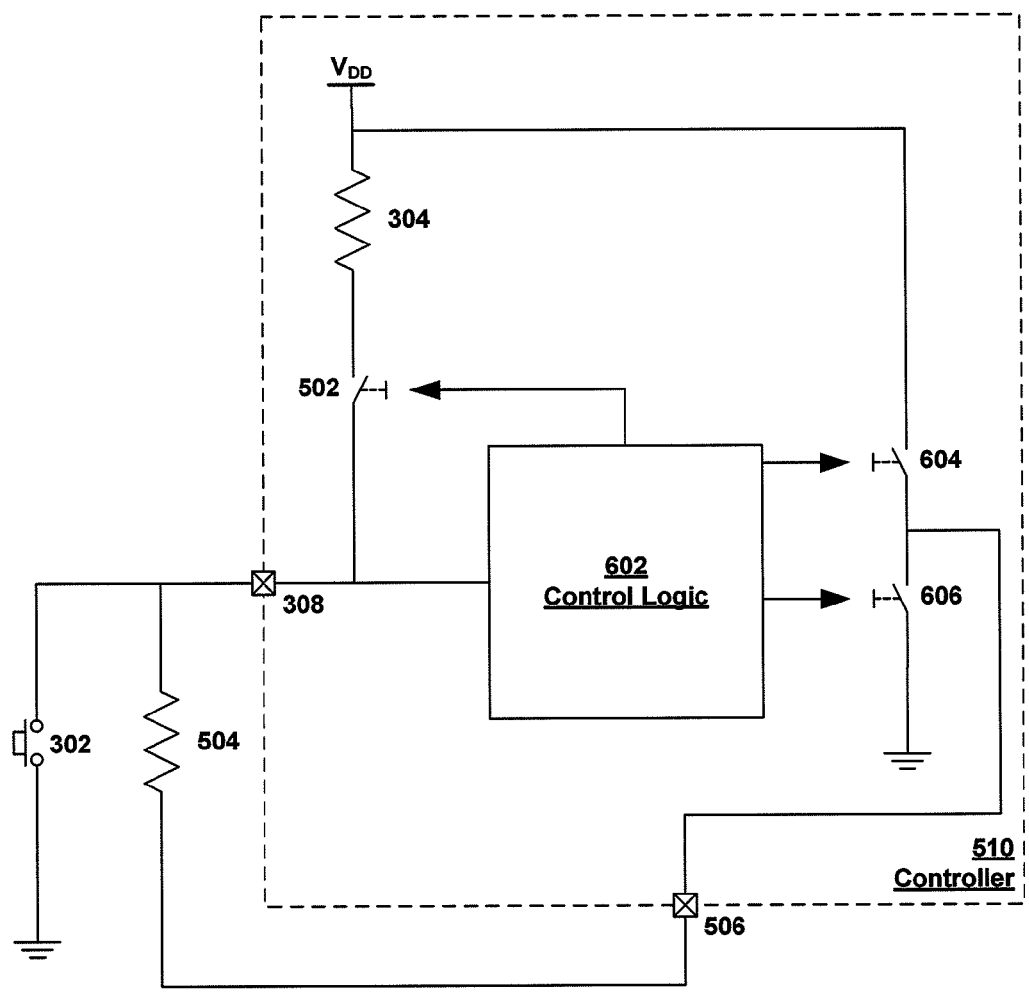
FIG. 6 is an exemplary embodiment of a therapeutic agent delivery device with switch integrity testing.

FIG. 6 is an exemplary embodiment of a therapeutic agent delivery device with switch integrity testing. More specifically, controller 510 and more specifically integrity sublogic 512 (not shown) comprises switch 604 and switch 606 which are controlled by control logic 602. When switch 604 and switch 606 are open switch integrity test output 506 is left floating. When switch 604 is closed and switch 606 is open, switch integrity test output 506 provides a high supply voltage. When switch 604 is open and switch 606 is closed, switch integrity test output 506 provides a low supply voltage. Again, although $V_{DD}$ and ground are used for illustrative purposes in FIG. 6, any logical high ($V_H$) can be used instead of $V_{DD}$ and any logical low ($V_L$) can be used instead of ground. In some embodiments $V_H<V_{DD}$ or $V_L>$ ground. In some embodiments $V_H<V_{DD}$ and $V_L>$ ground.

Figure 7:
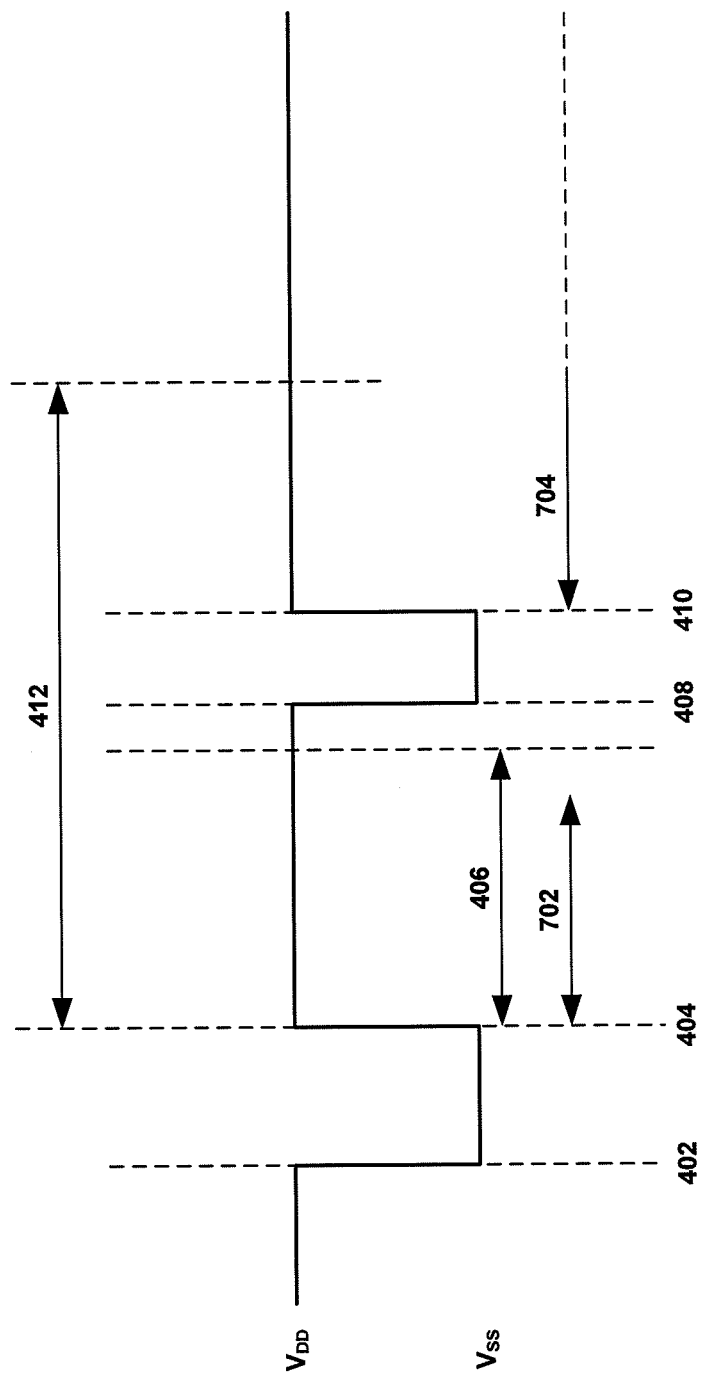
FIG. 7 shows exemplary timing of an activation sequence with switch integrity testing.

A variety of tests can be performed in this configuration. Referring to FIG. 7, due to the double button press safeguards against accidental dosing, there are several opportunities to apply switch integrity testing. After a button release at time 404, switch 302 is ignored until predetermined minimum time interval 406 has elapsed, during this period the integrity of switch 302 and its interfaces can be tested. As long as the test takes less than the minimum time interval 406, a short test (e.g. a fast analog test or a digital test) can be performed. In some embodiments, a fast analog test is performed. Depicted in FIG. 7 is time span 702 which is the time a short test can be performed. After the second button release at time 410, another test (e.g. a digital or a fast or slow analog test) can take place during the delivery of the therapeutic agent, because during this period of time any signal by switch 302 can be ignored. The second test is depicted in FIG. 7 during time span 704. Again, although $V_{DD}$ and $V_{SS}$ are used for illustrative purposes in FIG. 7, any logical high ($V_H$) can be used instead of $V_{DD}$ and any logical low ($V_L$) can be used instead of $V_{SS}$. In some embodiments $V_H<V_{DD}$ or $V_L>V_{SS}$. In some embodiments $V_H<V_{DD}$ and $V_L>V_{SS}$.

Figure 8:
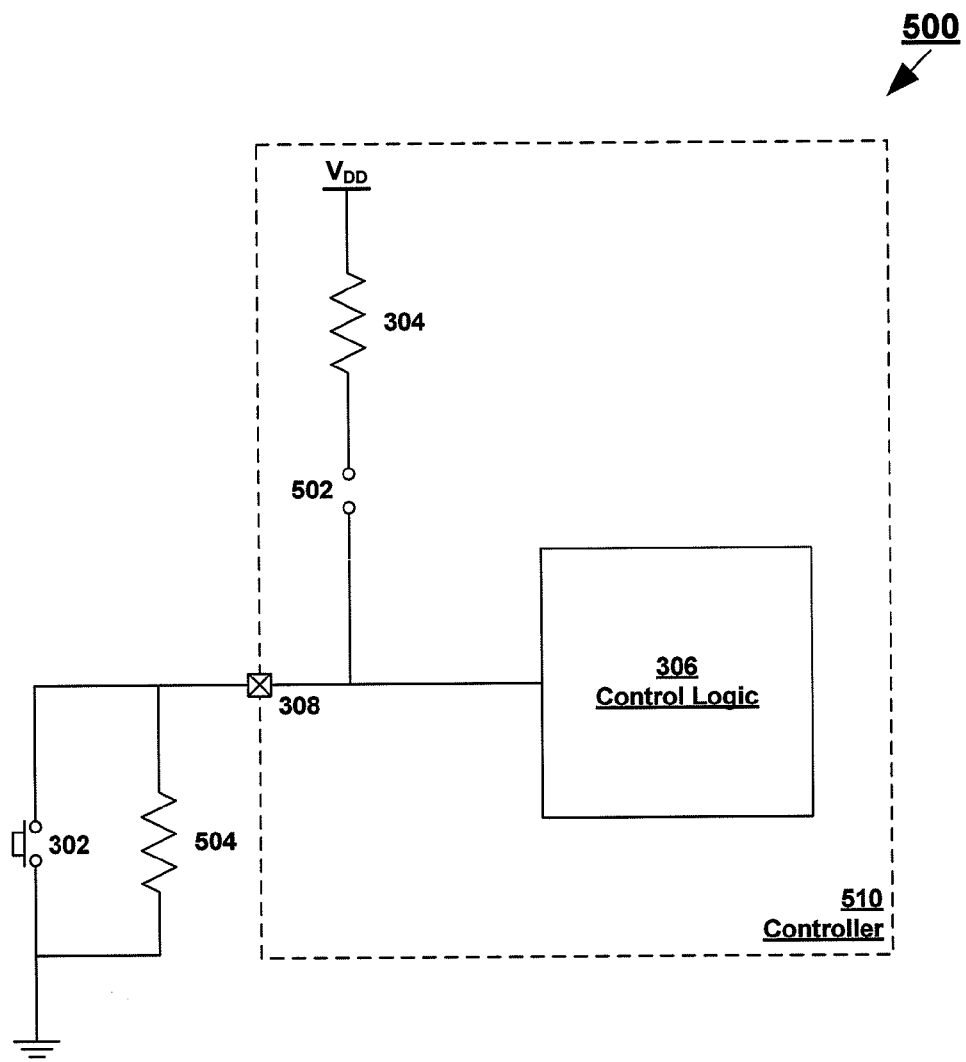
FIG. 8 shows an equivalent circuit configuration of therapeutic agent delivery device 500 during a short interval switch grounding integrity test.

FIG. 8 shows an equivalent circuit configuration of therapeutic agent delivery device 500 during a short interval switch grounding integrity test. During the short interval switch test, switch integrity test output 506 is forced from a high supply voltage state to a low supply voltage state, depicted in FIG. 8 as grounding resistor 504. Additionally switch 502 is opened during the test. During the test resistor 504 acts as a pull down resistor causing the voltage at switch input 308 to drop from $V_{DD}$ to $V_{SS}$. The rate at which the voltage falls is based on the resistance-capacitance ("RC") time constant. The resistance in the circuit is furnished by resistor 504 and the capacitance is the capacitance inherent in switch input 308 and circuitry. For example, if controller 510 is implemented in an ASIC mounted to a printed circuit board (PCB), metal traces in the PCB, interface pins, balls or lands in the ASIC package can be major sources of capacitance. Due to experimentation, a nominal capacitance of controller 510 can be determined. Any deviation in the observed decay rate of the voltage seen at switch input 308 can result from resistor 504 being bad, contamination, shorts, open circuits ("opens"), missing or bad PCB traces, or a bad ASIC interface. For example, electrostatic discharge (ESD) during manufacturing, packaging, storage or use could damage the ASIC interface. Again, although $V_{DD}$ and ground are used for illustrative purposes in FIG. 8, any logical high ($V_H$) can be used instead of $V_{DD}$ and any logical low ($V_L$) can be used instead of ground. In some embodiments $V_H<V_{DD}$ or $V_L>$ ground. In some embodiments $V_H<V_{DD}$ and $V_L>$ ground.

Figure 9:
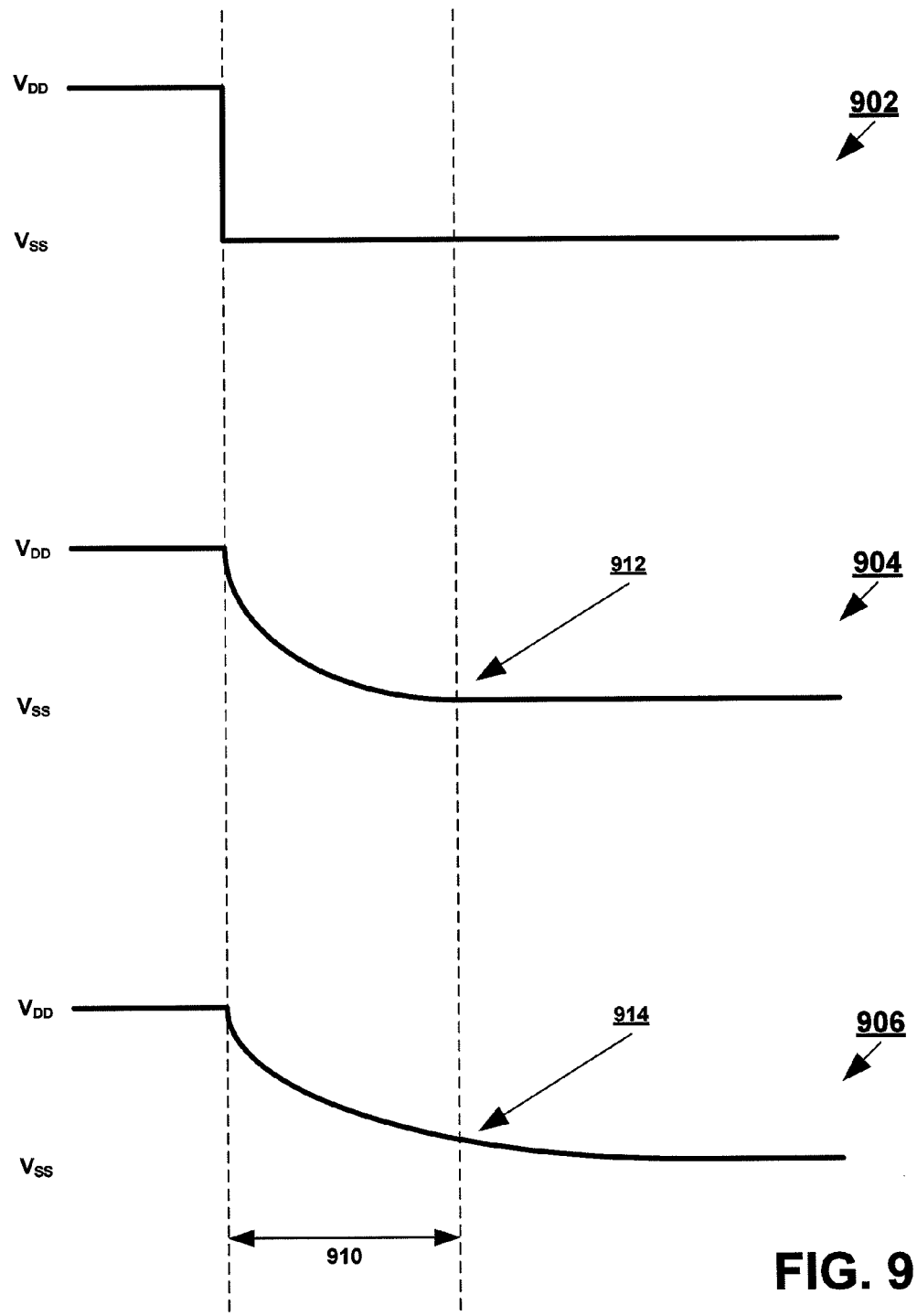
FIG. 9 shows signaling during the short interval switch grounding integrity test.

FIG. 9 shows signaling during the short interval switch grounding integrity test. Signal trace 902 is the signal from integrity switch test output 506 which initially begins at $V_{DD}$ and drops abruptly to $V_{SS}$. Signal trace 904 is the signal observed at switch input 308 for a "good" therapeutic agent delivery device. After predetermined time interval 910 has elapsed after the drop in the voltage of integrity switch test output 506, the signal has decayed to a known value as indicated by arrow 912. However, if the after predetermined time interval 910, the signal as shown by signal trace 906 observed at switch input 308 does not decay as rapidly as expected, to the known value as indicated by arrow 914, there may be excess capacitance or resistance in the test circuit which could indicate the existence of a fault or a precursor of a fault as described above. Again, although $V_{DD}$ and $V_{SS}$ are used for illustrative purposes in FIG. 9, any logical high ($V_H$) can be used instead of $V_{DD}$ and any logical low ($V_L$) can be used instead of $V_{SS}$. In some embodiments $V_H<V_{DD}$ or $V_L>V_{SS}$. In some embodiments $V_H<V_{DD}$ and $V_L>V_{SS}$.

Figure 10:
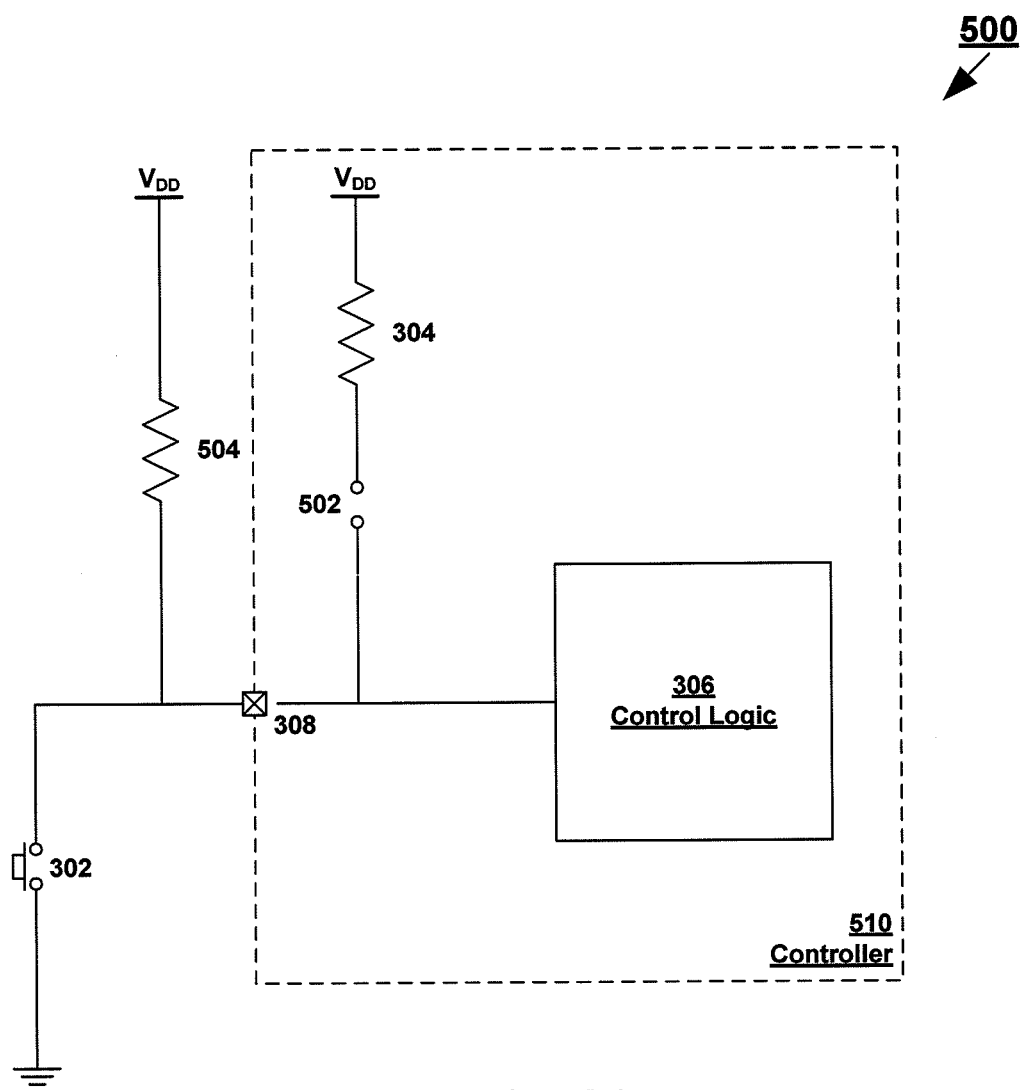
FIG. 10 shows an equivalent circuit configuration of therapeutic agent delivery device 500 during a short interval power switch integrity test.

FIG. 10 shows an equivalent circuit configuration of therapeutic agent delivery device 500 during a short interval power switch integrity test. During the short interval switch test, switch integrity test output 506 is forced from a low supply voltage state to a high supply voltage state, depicted in FIG. 10. Once again switch 502 is opened during the test. During the test, resistor 504 acts as a pull up resistor causing the voltage at switch input 308 to rise from $V_{SS}$ to $V_{DD}$. The rate at which the voltage rises is based on the RC time constant, similar to that described above for the short interval switch grounding integrity test. Once again, the causes of deviation from the nominal RC time constant described above can result from resistor 504 being bad, contamination, shorts, opens, missing or bad PCB traces, or a bad ASIC interface. Again, although $V_{DD}$ and ground are used for illustrative purposes in FIG. 10, any logical high ($V_H$) can be used instead of $V_{DD}$ and any logical low ($V_L$) can be used instead of ground. In some embodiments $V_H<V_{DD}$ or $V_L>$ ground. In some embodiments $V_H<V_{DD}$ and $V_L>$ ground.

Figure 11:
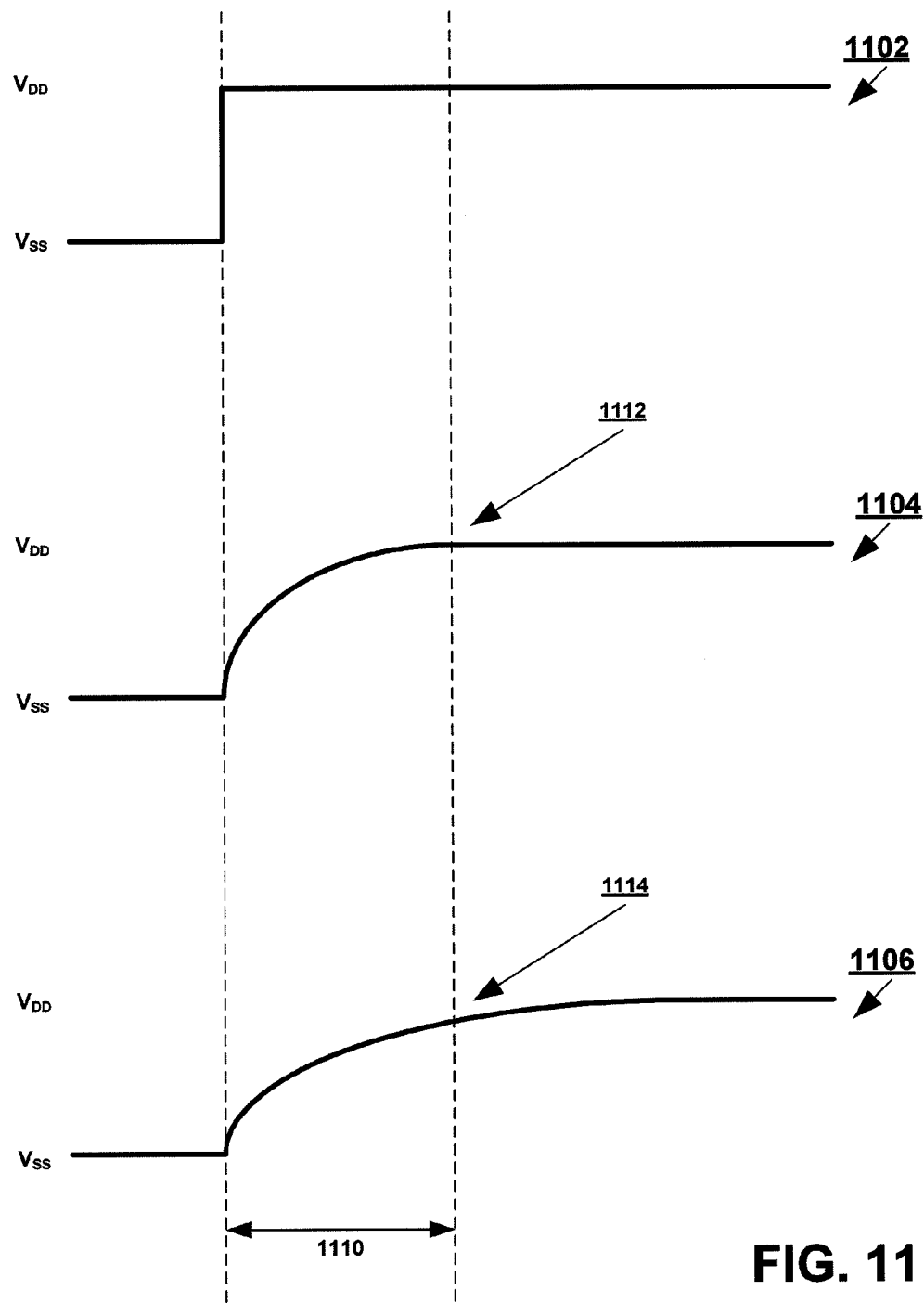
FIG. 11 shows signaling during the short interval power switch integrity test.

FIG. 11 shows signaling during the short interval power switch integrity test. The signal is logically complementary to that depicted in FIG. 9. Signal trace 1102 is the signal from integrity switch test output 506 which initially begins at $V_{SS}$ and rises abruptly to $V_{DD}$. Signal trace 1104 is the signal observed at switch input 308 for a "good" therapeutic agent delivery device. After predetermined time interval 1110 has elapsed after the drop in the voltage of integrity switch test output 506, the signal has risen to a known value as indicated by arrow 1112. However, if the after predetermined time interval 910, the signal as shown by signal trace 906 observed at switch input 308 does not rise as rapidly as expected, to the known value as indicated by arrow 1114, there may be excess capacitance or resistance in the test circuit which could indicate the existence of a fault or a precursor of a fault as described above. It is noted that where testing is conducted after a second button push, e.g. as in some embodiments employing digital testing, there need not be any timing element; and in some such embodiments there is no timing element. Again, although $V_{DD}$ and $V_{SS}$ are used for illustrative purposes in FIG. 11, any logical high ($V_H$) can be used instead of $V_{DD}$ and any logical low ($V_L$) can be used instead of $V_{SS}$. In some embodiments $V_H<V_{DD}$ or $V_L>V_{SS}$. In some embodiments $V_H<V_{DD}$ and $V_L>V_{SS}$.

Figure 12:
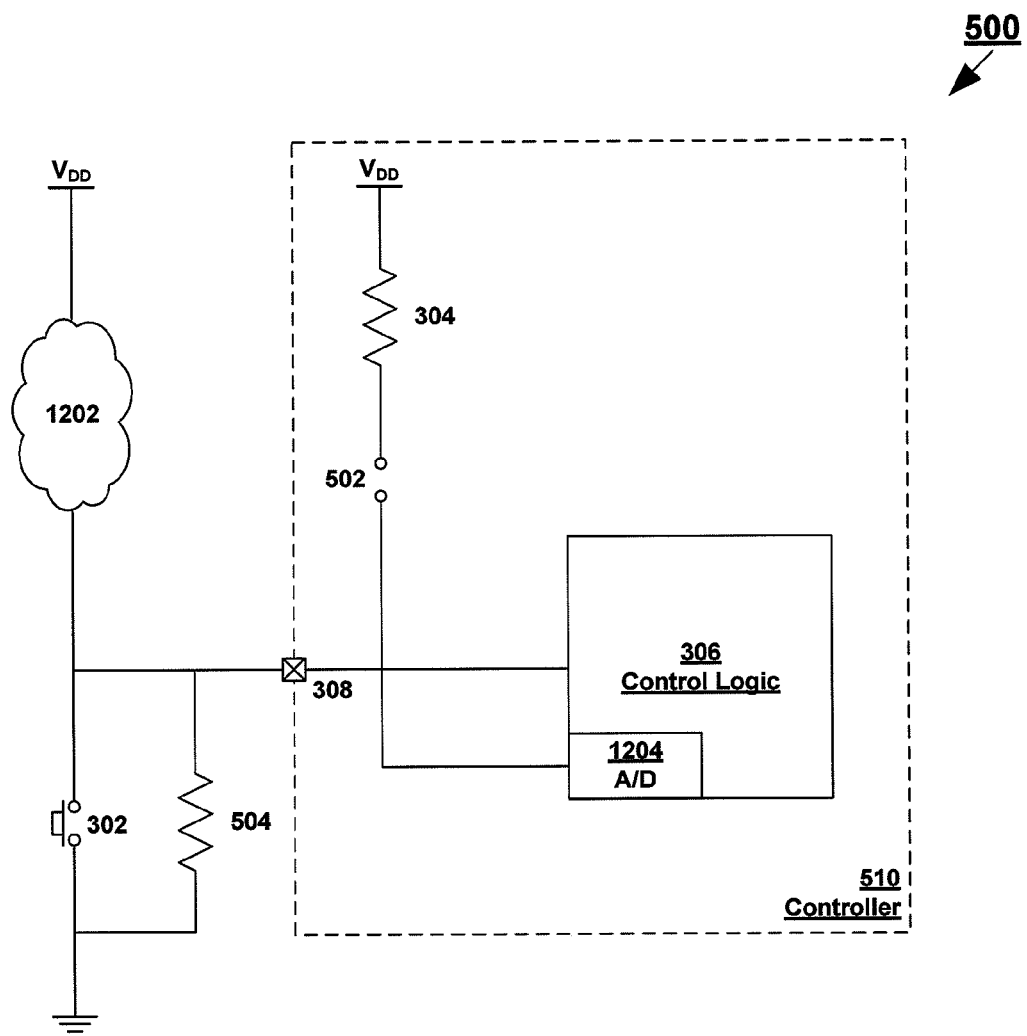
FIG. 12 shows an equivalent circuit configuration of therapeutic agent delivery device 500 during a long interval analog switch grounding integrity test.

FIG. 12 shows an equivalent circuit configuration of therapeutic agent delivery device 500 during an analog switch grounding integrity test. The equivalent circuit configuration shown in FIG. 12 is essentially the same configuration as that depicted in FIG. 8. Additionally control logic 306 further comprises a means for measuring the voltage at switch input 308. In the depicted embodiment, the means for measuring voltage is analog to digital converter ("ADC") 1204, however other methods for measuring voltage can be implemented, such as the use of a set of comparator circuits in place of the ADC to measure the voltage level of the analog signal compared to a comparator threshold. As in FIG. 8, switch integrity test output 506 is forced down to a low supply voltage state, so resistor 504 acts as a pull down resistor. If contamination or corrosion (shown as 1202) exists between switch 302, switch input 308 or connecting wirings and a high power supply source such as a power line metal trace, the contamination or corrosion may act as a resistor pulling up against resistor 504 resulting in a voltage divider. The result is that resistor 504 would not be able to completely pull down the voltage at switch input 308 down to $V_{SS}$. If the voltage that switch input 308 fails to settle at $V_{SS}$, then contamination, corrosion or other corruption of the apparatus is causing a short between the switch 302 and/or switch input 308 and a high power supply source. Again, although $V_{DD}$ and $V_{SS}$ are used for illustrative purposes in FIG. 12, any logical high ($V_H$) can be used instead of $V_{DD}$ and any logical low ($V_L$) can be used instead of $V_{SS}$. In some embodiments $V_H<V_{DD}$ or $V_L>V_{SS}$. In some embodiments $V_H<V_{DD}$ and $V_L>V_{SS}$.

Figure 13:
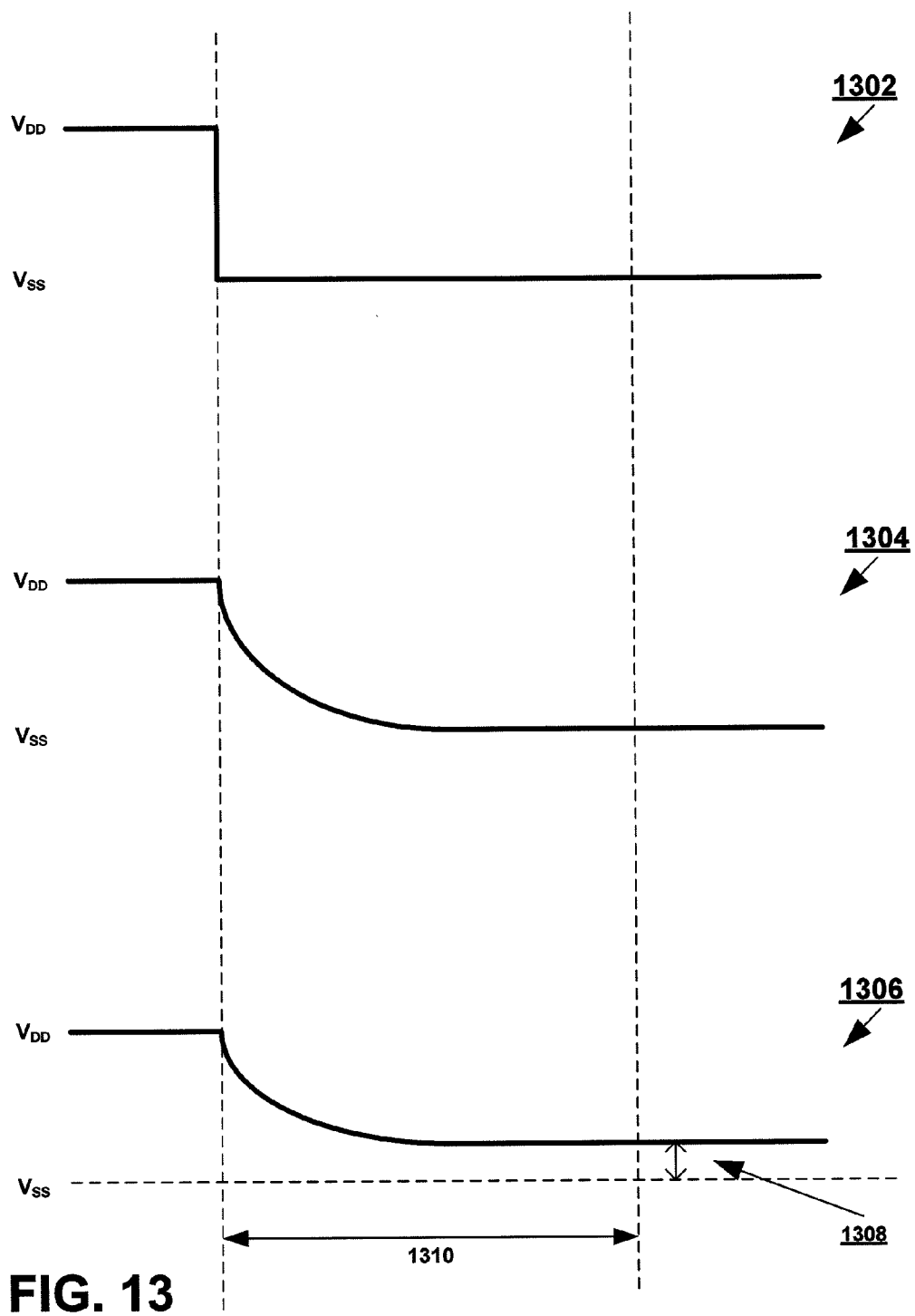
FIG. 13 shows signaling during the long interval analog switch grounding integrity test.

FIG. 13 shows signaling during the long interval analog switch grounding integrity test. (Although reference is made to a long interval analog grounding integrity test, the test may be made short interval by adjusting the number of data points collected.) Signal trace 1302 is the signal from integrity switch test output 506 which initially begins at $V_{DD}$ and drops abruptly to $V_{SS}$. Signal trace 1304 is the signal observed at switch input 308 for a "good" therapeutic agent delivery device. After predetermined time interval 1310 has elapsed after the drop in the voltage of integrity switch test output 506, the signal has decayed to its final value. Predetermined interval 1310 differs from predetermined interval 910 shown in FIG. 9. Because the objective of the short interval test is to measure the rate of decay, predetermined interval 910 should be short enough so that any change in the RC time constant would be observed. In contrast, predetermined interval 1310 should be long enough so that the signal observed at switch input 308 should have decayed to a steady state voltage regardless of the RC time constant (or at least within a reasonable range of RC time constants). Signal trace 1306 is the signal observed at switch input 308 for a therapeutic delivery agent when corruption or some other source causes a short between a high power supply and switch 302 and/or switch input 308. The discrepancy between the steady state voltage and $V_{SS}$ is indicated by arrow 1308. Again, although $V_{DD}$ and $V_{SS}$ are used for illustrative purposes in FIG. 13, any logical high ($V_H$) can be used instead of $V_{DD}$ and any logical low ($V_L$) can be used instead of $V_{SS}$. In some embodiments $V_H<V_{DD}$ or $V_L>V_{SS}$. In some embodiments $V_H<V_{DD}$ and $V_L>V_{SS}$.

Operationally, after predetermined time interval 1310, control logic 306 measures the voltage at switch input 308. If the steady state voltage exceeds a given threshold, a fault can be indicated by controller 510. Additionally or alternatively, if the steady state voltage exceeds a second threshold a precursor to a fault can be indicated and appropriate action can be taken by controller 510.

Figure 14:
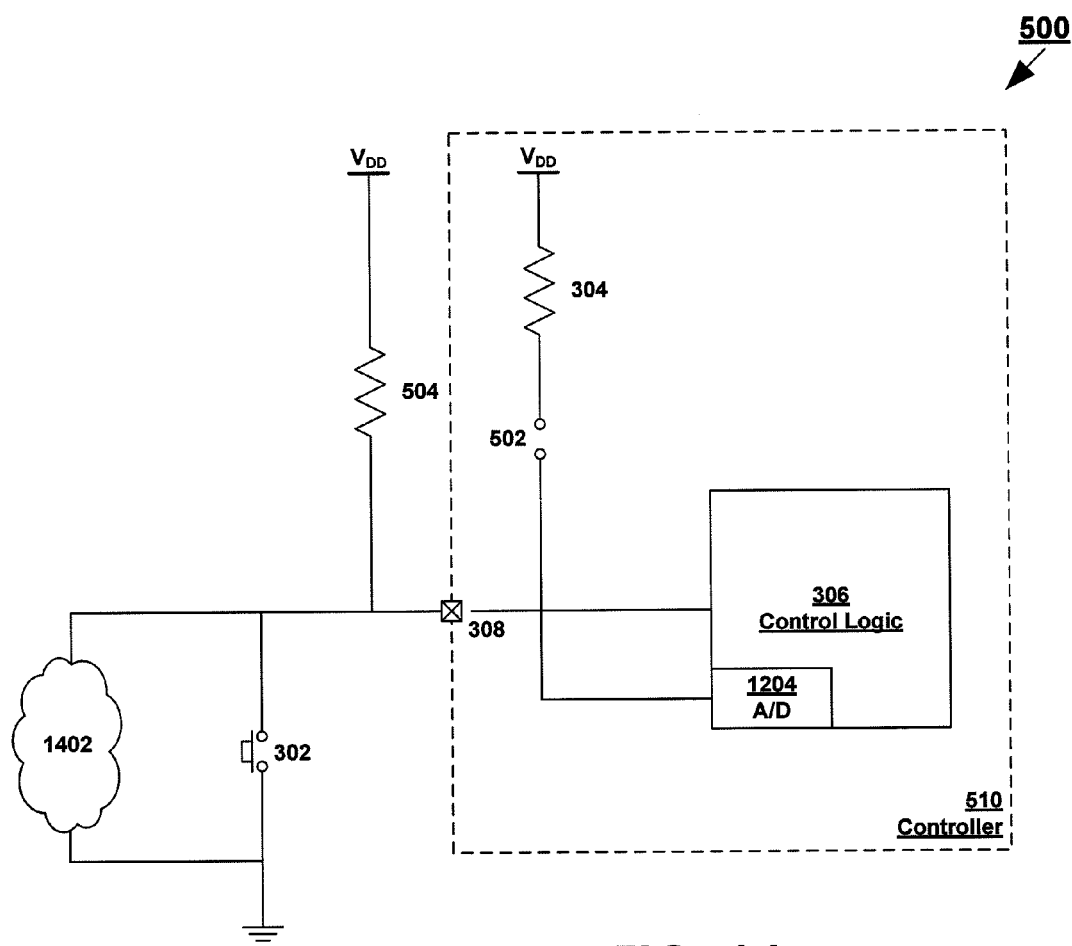
FIG. 14 shows an equivalent circuit configuration of therapeutic agent delivery device 500 during a long interval analog power switch integrity test.

FIG. 14 shows an equivalent circuit configuration of therapeutic agent delivery device 500 during a long interval analog power switch integrity test. The equivalent circuit configuration shown in FIG. 14 is essentially the same configuration as that depicted in FIG. 10. Once again control logic 306 further comprises a means for measuring the voltage at switch input 308. As in FIG. 10, switch integrity test output 506 is forced up to a high supply voltage state, so resistor 504 acts as a pull up resistor. If contamination or corrosion (shown as 1402) exists between switch 302, switch input 308 or connecting wirings and a low power supply source such as a ground trace, or if contamination or corrosion intrudes between the two poles on switch 302 causing switch 302 to short, the contamination or corrosion may act as a resistor pulling down against resistor 504 resulting in a voltage divider. The result is that resistor 504 would not be able to completely pull up the voltage at switch input 308 up to $V_{DD}$. If the voltage that switch input 308 fails to settle at $V_{DD}$, then contamination, corrosion or other corruption of the apparatus is causing a short to a low power supply source. Again, although $V_{DD}$ and $V_{SS}$ are used for illustrative purposes in FIG. 14, any logical high ($V_H$) can be used instead of $V_{DD}$ and any logical low ($V_L$) can be used instead of $V_{SS}$. In some embodiments $V_H < V_{DD}$ or $V_L > V_{SS}$. In some embodiments $V_H < V_{DD}$ and $V_L > V_{SS}$.

Figure 15:
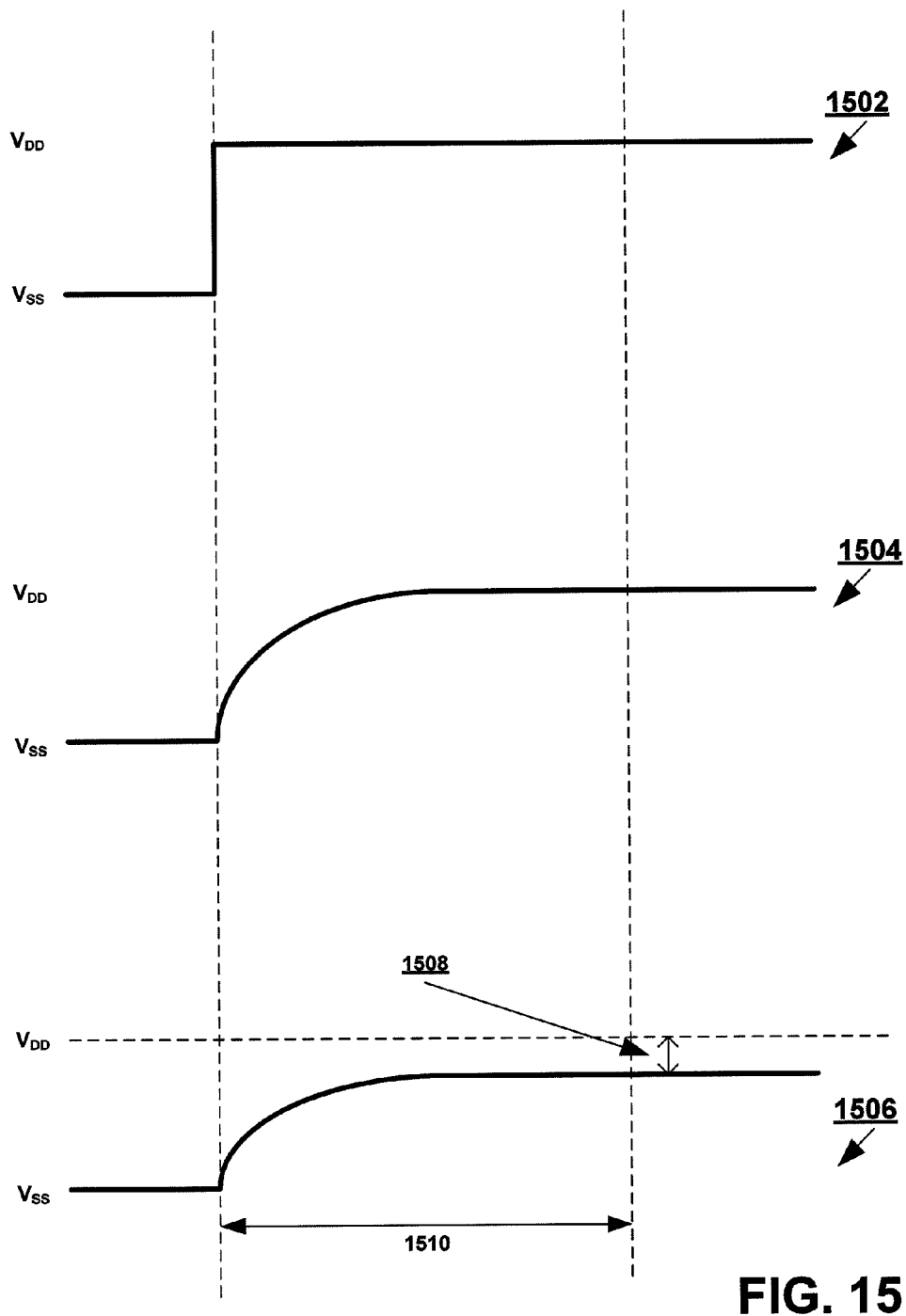
FIG. 15 shows signaling during the long interval analog power switch integrity test.

FIG. 15 shows signaling during the long interval analog power switch integrity test. Signal trace 1502 is the signal from integrity switch test output 506 which initially begins at $V_{SS}$ and rises abruptly to $V_{DD}$. Signal trace 1504 is the signal observed at switch input 308 for a "good" therapeutic agent delivery device. After predetermined time interval 1510 has elapsed after the rise in the voltage of integrity switch test output 506, the signal has risen to its final value. Once again, predetermined interval 1510 differs from predetermined interval 1110 shown in FIG. 11, for reasons similar to the difference between predetermined interval 1310 and predetermined interval 910. Signal trace 1506 is the signal observed at switch input 308 for a therapeutic delivery agent when corruption or some other source causes a short between a low power supply and switch 302 and/or switch input 308. The discrepancy between the steady state voltage and $V_{DD}$ is indicated by arrow 1508. Again, although $V_{DD}$ and $V_{SS}$ are used for illustrative purposes in FIG. 15, any logical high ($V_H$) can be used instead of $V_{DD}$ and any logical low ($V_L$) can be used instead of $V_{SS}$. In some embodiments $V_H < V_{DD}$ or $V_L > V_{SS}$. In some embodiments $V_H < V_{DD}$ and $V_L > V_{SS}$.

Operationally, after predetermined time interval 1510, control logic 306 measures the voltage at switch input 308. If the voltage differential between the steady state voltage and $V_{DD}$ exceeds a given threshold, a fault can be indicated by controller 510. Additionally or alternatively, if the voltage differential exceeds a second threshold a precursor to a fault can be indicated and appropriate action can be taken by controller 510.

Figure 16:
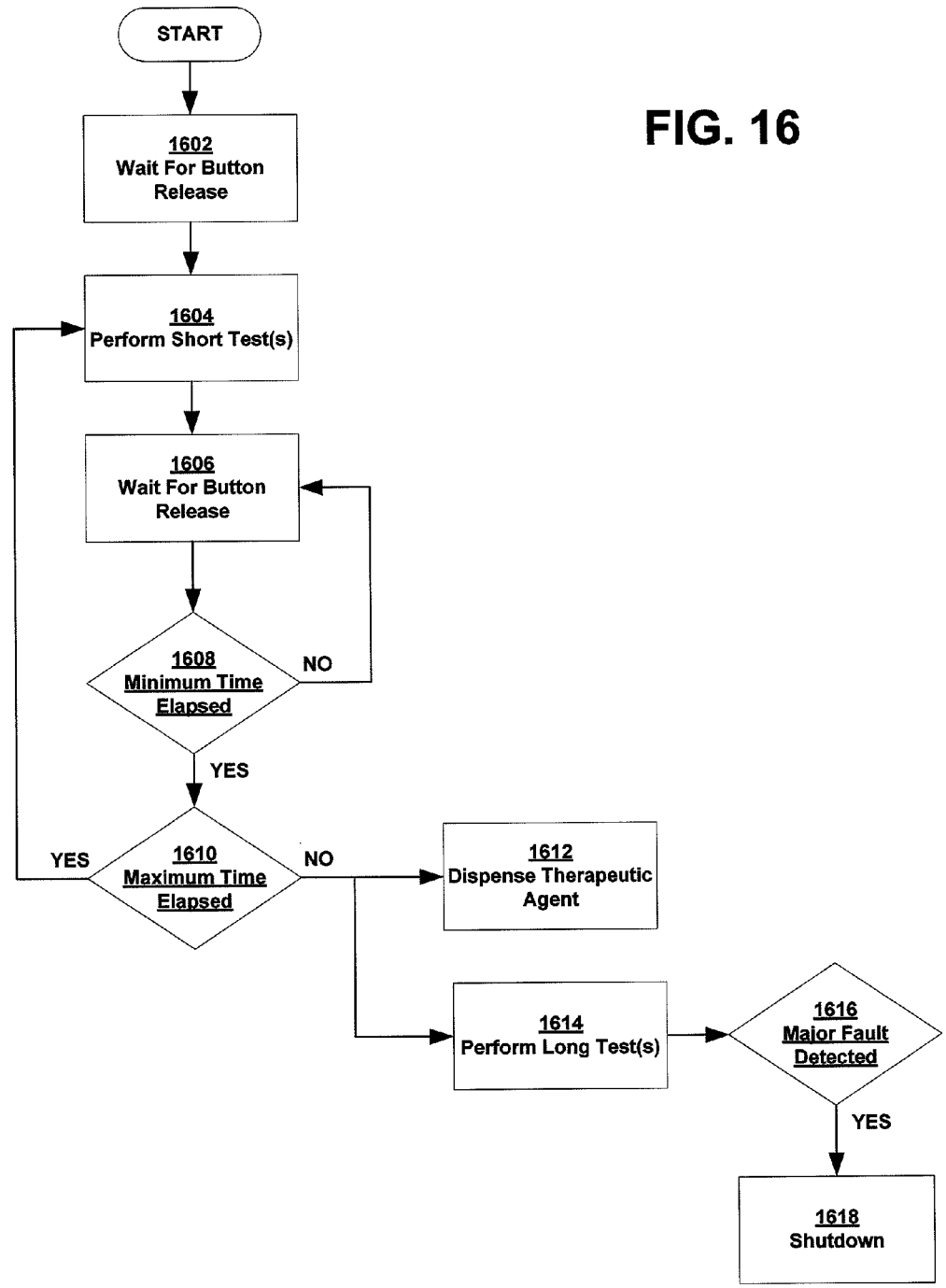
FIG. 16 shows a flow chart of the dosing operation of an embodiment of a therapeutic agent delivery device with switch integrity testing.

FIG. 16 shows a flow chart of the dosing operation of an embodiment of a therapeutic agent delivery device with switch integrity testing. At step 1602, the device waits for a button release. This corresponds to waiting for event 404 in FIG. 7. At step 1604 after the button has been released one or more short switch integrity tests can be performed such as those described above in FIGS. 8-11. At step 1606, the device waits for a second button release. After the button has been released, at step 1608, a determination is made as to whether the second button press has occurred within the predetermined minimum time interval. If it has not, the last button release is ignored and the device returns to step 1606 where it waits for another button release. If it has, a determination is made as to whether the maximum time interval since the first button release has elapsed. If it has, the second button release is treated as the first hence the device returns to step 1604. If the maximum time has not elapsed, at step 1612, delivery of the therapeutic agent begins. (Although not specifically depicted in FIG. 16, it is to be understood that one or more switch integrity checks may be performed between step 1610 and step 1612, such as a digital switch integrity check or a fast analog integrity check.) Concurrently with delivery of therapeutic agent, the device can perform one or more optional long switch integrity tests at step 1614. Concurrently, a determination is made at step 1616 as to whether a fault with sufficient severity to warrant the shutdown of the device has occurred. If so the device shuts down at step 1618.

Figure 17:
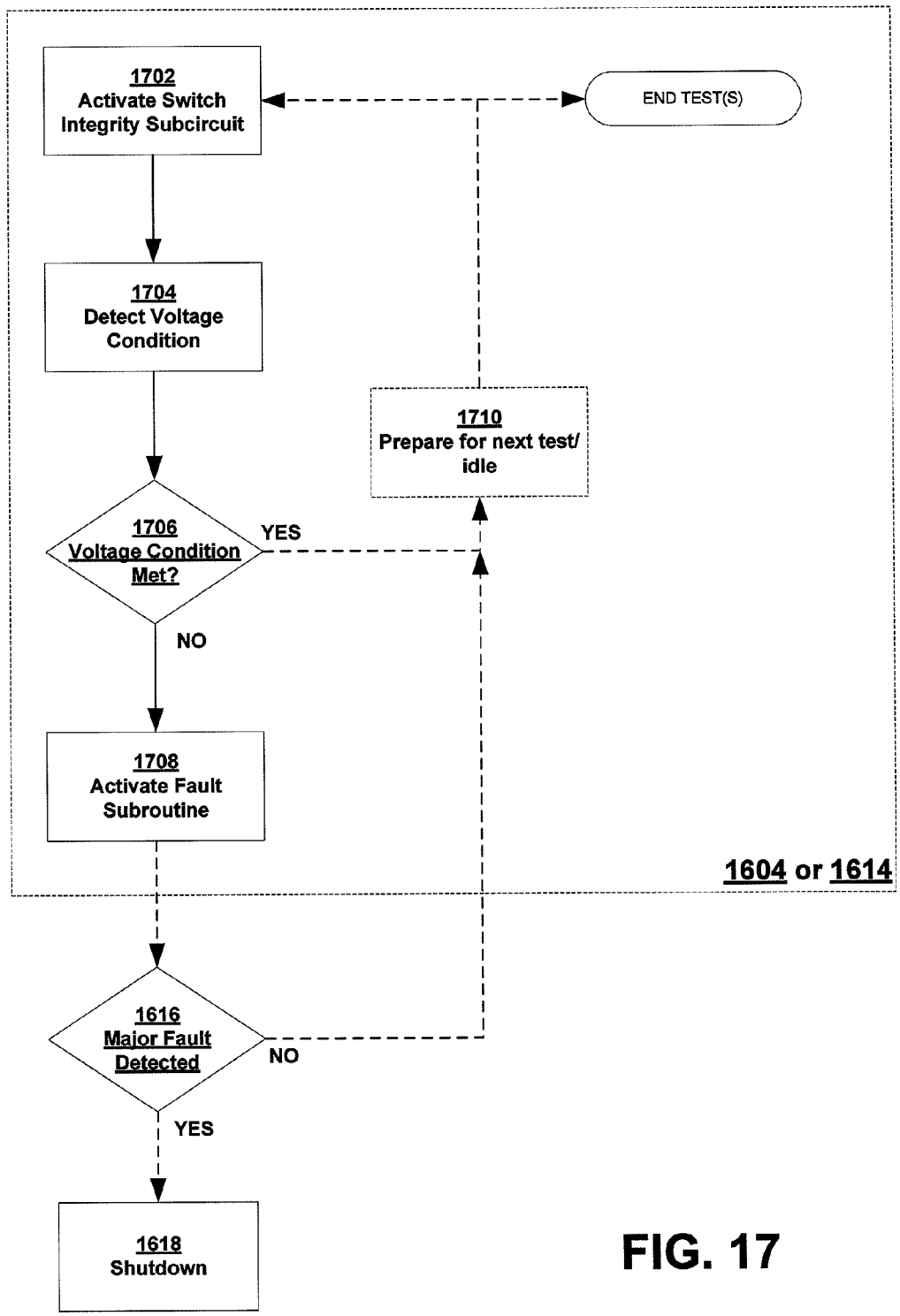
FIG. 17 shows an exemplary embodiment of a switch integrity testing process.

FIG. 17 shows exemplary embodiment of a switch integrity testing process. The flowchart shown is representative of typical switch integrity processes which be used in steps 1604 and/or step 1614. At step 1702, device 500 activates its switch integrity subcircuit. In the examples given above, this can include opening switch 502, setting the switch integrity test output to a predetermined voltage such as $V_{DD}$ or $V_{SS}$ and/or optionally powering on or activating ADC 1204 such as in the configurations shown in FIGS. 12 and 14. In some embodiments, the ADC circuitry could be powered off when not testing to save power. At step 1704, one or more predetermined voltage conditions are tested for. Examples of these conditions are described above in FIGS. 8-15. For example, in the short tests described in FIGS. 8-11, after a predetermined time interval has elapsed after the switch integrity test output is set to the predetermined voltage, the voltage at switch input 308 is measured. If the measured voltage has risen or decayed to the expected voltage, a voltage condition is deemed to be detected. In another example, in the long tests described in FIG. 12-16, after a predetermined time interval has elapsed after the switch integrity test output is set to the predetermined voltage, the voltage at switch input 308 is measured. If a discrepancy exists between the predetermined voltage and the measured voltage then a voltage condition is deemed to be detected.

At step 1706 a determination is made as to whether a predetermined voltage condition was detected, if so at step 1708 a fault subroutine is activated. More specifically, each predetermined voltage condition is associated with a fault or a precursor to a fault. The fault subroutine can take one or more courses of action depending on the severity of the fault or precursor to a fault. For example, the patient or care provider can be alerted by activating a user alert feature. As previously discussed, the user alert feature can include a variety of means to alert a user that operation of the system is considered compromised. In some embodiments, the device is configured to detect precursors to faults, so the device may activate the user alert even before a fault has been detected that would cause an effect that would be experienced by the patient. The user alert may be an indicator light, such as a colored light emitting diode (LED), an audible tone (such as a repeating "beep"), a readable display (such as a liquid crystal display (LCD)), other user observable indicator, communications to an external monitoring device, (e.g., a wireless transmission to a central console) or combinations of two or more thereof.

In another example, the faults and precursors to faults can be logged in memory. In some such embodiments, the controller detects a certain type of fault, assigns it a fault code, and records the fault code in memory for retrieval at a later time. For instance, the controller may detect and record one of the following conditions: a low voltage at a point and under conditions where a high voltage would be expected for a normally operating circuit; a voltage at a point and under conditions that is higher or lower than the voltage that would be expected for a normally operating circuit; a voltage rise time that is longer or shorter than would be expected for a normally operating circuit; a voltage or current fall time that is longer or shorter than would be expected for a normally operating circuit; or combinations of two or more thereof. The logs can be retrieved in several ways, for example it may be retrieved by a removable memory medium such as flash memory, viewed by a care provider by one or more visual messages on a display device, or transmitted to an external monitoring device.

In another example, when the faults have sufficient severity pose a risk to a patient, the device can be deactivated such as by irreversibly decoupling the voltage supply from the drug delivery circuit, shorting a power cell to ground, fusing a fusible link in the circuit, by means of software logic, etc., as described herein.

In another example, the fault subroutine can perform a combination of the actions described. For example, initially, precursors to faults are logged, but as the severity of the potential faults increases, a user alert is issued. Finally, when potential faults become actual faults and the severity is sufficiently high, the device shuts down at step 1618.

If no voltage condition is found at step 1706 or after the voltage condition is processed at step 1708, optionally the switch integrity process can proceed to step 1710 where either the device prepares for the next test or prepares to end the final test. In the former case, the device may set the switch integrity test output to another voltage. For example, in preparation for one of the grounding tests described above in FIGS. 8-9, 12-13, the switch integrity test output could be set to $V_{DD}$ so that when the grounding tests begins in step 1702 the switch integrity test output can be driven down to $V_{SS}$ to initiate the test. However, this can be minimized by proper selection of tests. For example, if the power tests and the ground tests are alternated, there is no need to set the switch integrity test output to another voltage as each tests leaves the switch integrity test output in the appropriate voltage to initiate the other test. In the latter case at step 1710, the device can deactivate the switch integrity subcircuit, for example the switch integrity test output can be set to its non-test default state which can be either the high supply voltage or the low supply voltage. Alternatively, the switch integrity test output could be left floating. Additionally switch 502 is closed so that resistor 304 can resume its pull up function.

While preferred embodiments of the present invention have been shown and described herein, those skilled in the art will recognize that such embodiments are provided by way of example only. Numerous variations, changes, and substitutions will now occur to those skilled in the art without departing from the invention. It should be understood that various alternatives to the embodiments of the invention described herein may be employed in practicing the invention. It is intended that the following claims define the scope of the invention and that methods and structures within the scope of these claims and their equivalents be covered thereby.

What is claimed is:

1. A switch operated medical device, comprising:
   a use-actuated device switch configured to be actuated by a user, which provides a switch signal to a switch input of a device controller when actuated by a user;
   the device controller configured to actuate the device after the user presses the device switch at least two times within a predetermined interval, the device controller further having said switch input operatively connected to the device switch, and configured to receive the switch signal from the device switch, the device controller being configured to actuate the device after a second push of the device switch when the switch signal meets certain predetermined conditions; and
   a switch integrity test sub circuit, which is configured to detect a fault or a precursor to a fault in the device switch by determining an evoked response at the switch input after release of the device switch but before the second push of the device switch, when the controller sets the switch input to one or more predetermined voltages to evoke a response, and comparing the evoked response to one or more expected values, and causing the controller to execute a switch fault subroutine when a fault or a precursor to a fault is detected.

2. The device of claim 1, wherein the switch integrity test sub circuit is configured to check for and detect a fault or a precursor to a fault in the device switch.

3. The device of claim 1, wherein the switch integrity test subcircuit is configured to test for and detect at least one fault or precursor to a fault selected from the group consisting of contamination, short circuits (including intermittent short circuits), compromised circuit components (including malfunctioning resistors, integrated circuit pins, and/or capacitors), particulates, solder balls, or combinations of two or more thereof.

4. The device of claim 1, wherein the switch integrity test subcircuit is configured to test for and detect a voltage or change in voltage in between a short between the switch input and ground, a short between the switch input and a voltage pull up, a damaged circuit resistor, contamination, corrosion or a damaged integrated circuit pin.

5. The device of claim 1, wherein the switch fault subroutine includes at least one of: activating a user alert feature, logging detection of faults or precursors to faults, deactivating the device, or one or more combinations thereof.

6. The device of claim 1, wherein the controller is configured to measure a voltage or a rate of change of voltage at the switch input and executing the switch fault subroutine when the voltage or rate of change of voltage at the switch input fails to meet one or more predetermined parameters.

7. The device of claim 1, wherein the device is an iontophoresis delivery device comprising first and second electrodes and reservoirs, at least one of the reservoirs containing therapeutic agent to be delivered by iontophoresis, the device switch being operable by the user to actuate the device controller to provide power to the electrodes and deliver the therapeutic agent from the at least one of the reservoirs.

8. The device of claim 7, wherein the therapeutic agent is fentanyl, sufentanil, an opioid agent or an analog, derivative or salt of any of the foregoing.

9. The device of claim 8, wherein the therapeutic agent is fentanyl, sufentanil, carfentanil, lofentanil, alfentanil, hydromorphone, oxycodone, propoxyphene, pentazocine, methadone, tilidine, butorphanol, buprenorphine, levorphanol, codeine, oxymorphone, meperidine, dihydrocodeinone, cocaine, or an analog, pharmaceutically acceptable salt, ester or derivative thereof.

10. The device of claim 1, wherein the switch input is pulled up to a high voltage when the device switch is open and the switch input is a low voltage when the device switch is closed.

11. The device of claim 1, wherein the switch integrity test sub circuit is configured to perform both digital and analog testing.

12. The device of claim 1, wherein the controller is configured to set the switch input to a variety of test voltages or changes in voltage when the device switch is open to test the device switch and electronic circuitry without actuating the device.

13. The device of claim 1, wherein the switch integrity test sub circuit is part of the controller.

14. A method of switch fault detection in a switch operated medical device, said device comprising:
   a user-actuated device switch connected to a switch input of a device controller;
   the device controller comprising said switch input and configured to actuate the device after the user presses the device switch at least two times within a predetermined interval; and a switch integrity test sub circuit, said method comprising said controller:

setting the switch input to one or more predetermined voltages after release of the device switch but before a second push of the device switch;

activating the switch integrity test sub circuit;

detecting a voltage condition at the switch input; and activating a switch fault subroutine if the voltage condition at the switch input fails to meet one or more expected predetermined conditions.

15. The method of claim 14, wherein the steps of activating the switch integrity test subcircuit and detecting a voltage condition at the switch input are executed continuously throughout use of the device.

16. The method of claim 14, wherein the steps of activating the switch integrity test subcircuit and detecting a voltage condition at the switch input are executed periodically throughout use of the device.

17. The method of claim 14, wherein the switch fault subroutine includes at least one of: activating a user alert feature, logging detection of faults or precursors to faults, deactivating the device, or one or more combinations thereof.

18. The method of claim 14, wherein the voltage condition is a voltage, a change in voltage or both.

19. The method of claim 14, further comprising the controller detecting the voltage at the switch input under conditions in which the voltage should be zero or nearly zero if the switch integrity is within operating norms, and activating the switch fault subroutine if the voltage is significantly higher than zero.

20. The method of claim 14, further comprising the controller detecting the voltage at the switch input under conditions in which the voltage should be equal to a pull up voltage or nearly equal to the pull up voltage if the switch integrity is within operating norms, and activating the switch fault subroutine if the voltage is significantly lower than the pull up voltage.

21. The method of claim 14, further comprising the controller detecting a change in voltage at the switch input under conditions in which the voltage is expected to fall to zero or nearly to zero after within a predetermined period if the switch integrity is within operating norms, and activating the switch fault subroutine if the voltage fails to fall to zero or nearly to zero within the predetermined period.

22. The method of claim 14, further comprising the controller detecting a change in voltage at the switch input under conditions where the voltage should rise to a pull up voltage or nearly to the pull up voltage within a predetermined period if the switch integrity is within operating norms, and activating the switch fault subroutine if the voltage fails to rise to the pull up voltage or nearly to the pull up voltage within the predetermined period.

23. The method of claim 14, wherein the medical device is an iontophoresis delivery device comprising first and second electrodes and reservoirs, at least one of the reservoirs containing therapeutic agent to be delivered by iontophoresis, the device switch being operable by the user to actuate the device controller to provide power to the electrodes and deliver the therapeutic agent from the at least one of the reservoirs.

24. The method of claim 14, wherein the switch fault subroutine includes activating a user alert, deactivating the device, or both.

25. A switch operated medical device, comprising:

a use-actuated device switch configured to be actuated by a user, which provides a switch signal to a switch input of a device controller when actuated by a user;

the device controller configured to actuate the device after the user presses the device switch, the device controller further having said switch input operatively connected to the device switch, and configured to receive the switch signal from the device switch, the device controller being configured to actuate the device after the user pushes the device switch and when the switch signal meets certain predetermined conditions; and a switch integrity test sub circuit, which is configured to detect a fault or a precursor to a fault in the device switch by determining an evoked response at the switch input after release of the device switch but before 400 ms, when the controller sets the switch input to one or more predetermined voltages to evoke a response, and comparing the evoked response to one or more expected values, and causing the controller to execute a switch fault subroutine when a fault or a precursor to a fault is detected.

* * * * *